(12) United States Patent
Chang et al.

(10) Patent No.: US 9,226,494 B2
(45) Date of Patent: Jan. 5, 2016

(54) BIOREACTORS, SYSTEMS, AND METHODS FOR VASCULARIZING TISSUE CONSTRUCTS

(75) Inventors: Carlos C. Chang, Louisville, KY (US); James B. Hoying, Louisville, KY (US); Stuart K. Williams, Harrods Creek, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 697 days.

(21) Appl. No.: 12/562,832

(22) Filed: Sep. 18, 2009

(65) Prior Publication Data

US 2010/0075293 A1  Mar. 25, 2010

Related U.S. Application Data

(60) Provisional application No. 61/098,628, filed on Sep. 19, 2008, provisional application No. 61/221,153, filed on Jun. 29, 2009.

(51) Int. Cl.
*A01N 1/02* (2006.01)
*A01N 1/00* (2006.01)
(Continued)

(52) U.S. Cl.
CPC ............. *A01N 1/0247* (2013.01); *C12M 21/08* (2013.01); *C12M 23/38* (2013.01); *C12M 23/44* (2013.01); *C12M 25/14* (2013.01); *C12M 29/10* (2013.01)

(58) Field of Classification Search
CPC ..... A01N 1/0247; A01N 1/02; A01N 1/0231; C12M 21/08; C12M 29/10; C12M 23/44; C12M 25/14; C12M 23/38; C12M 25/02; C12M 27/14; C12M 37/04; C12M 41/46; B01J 19/0046; B82Y 30/00; G01N 33/5008; G01N 33/502; G01N 33/5038; G01N 33/5058; G01N 33/5064; G01N 33/5073
USPC .......................... 435/289.1, 1.2, 284.1, 293.1
See application file for complete search history.

(56) References Cited

U.S. PATENT DOCUMENTS 4,820,626 A   4/1989  Williams et al.
4,883,755 A   11/1989 Carabasi et al.
(Continued)

FOREIGN PATENT DOCUMENTS

EP       1500697    1/2005
WO       0078920    12/2000

OTHER PUBLICATIONS

Aper et al., "Autologous Blood Vessels Engineered From Peripheral Blood Sample," Eur J Vasc Endovasc Surg, 33, 2007, pp. 33-39.
(Continued)

*Primary Examiner* — William H Beisner
*Assistant Examiner* — Danielle Henkel
(74) *Attorney, Agent, or Firm* — Stites & Harbison, PLLC; Terry L. Wright

(57) ABSTRACT

A modular bioreactor is provided that includes an upper biochamber; a lower biochamber; and an intermediate biochamber that is positioned between the upper biochamber and the lower biochamber. Each biochamber of the bioreactor is in fluid communication with each other biochamber of the bioreactor and includes an interior wall, which defines a centrally-disposed cavity for each biochamber, and an inflow port and an outflow port that are in fluid communication with each centrally disposed cavity. Systems and methods for vascularizing a tissue construct are also provided.

25 Claims, 10 Drawing Sheets

(51) Int. Cl.
*C12M 1/00* (2006.01)
*C12M 3/00* (2006.01)
*C12M 1/12* (2006.01)

(56) References Cited

U.S. PATENT DOCUMENTS

| | | | |
|---|---|---|---|
| 4,963,489 A | 10/1990 | Naughton et al. | |
| 4,999,298 A | 3/1991 | Wolfe et al. | |
| 5,035,708 A | 7/1991 | Alchas et al. | |
| 5,190,878 A * | 3/1993 | Wilhelm | 435/297.2 |
| 5,516,681 A | 5/1996 | Naughton et al. | |
| 5,605,835 A | 2/1997 | Hu et al. | |
| 5,827,729 A | 10/1998 | Naughton et al. | |
| 5,957,972 A | 9/1999 | Williams et al. | |
| 6,197,575 B1 * | 3/2001 | Griffith et al. | 435/288.4 |
| 6,562,616 B1 * | 5/2003 | Toner et al. | 435/293.1 |
| 6,960,427 B2 | 11/2005 | Haverich et al. | |
| 7,029,838 B2 | 4/2006 | Williams et al. | |
| 7,052,829 B2 | 5/2006 | Williams et al. | |
| 7,122,371 B1 | 10/2006 | Ma | |
| 7,270,996 B2 | 9/2007 | Cannon et al. | |
| 7,371,400 B2 | 5/2008 | Borenstein et al. | |
| 2006/0188488 A1 | 8/2006 | Williams et al. | |
| 2006/0286664 A1 | 12/2006 | McAllister et al. | |
| 2007/0065933 A1 * | 3/2007 | Esser et al. | 435/286.6 |
| 2007/0275363 A1 * | 11/2007 | Bertram et al. | 435/1.2 |
| 2008/0075750 A1 * | 3/2008 | Akins | 424/423 |

OTHER PUBLICATIONS

Baumgartl et al., "Evaluation of PO(2) profiles to describe the oxygen pressure field within the tissue," Comparative Biochemistry and Physiology, 132, 2002, pp. 75-85.
Bishop, A., "Role of oxygen in wound healing," Journal of wound care, 17, 2008 pp. 399-402.
Cardinal et al., "Tissue-engineered Vascular Grafts as in Vitro Blood Vessel Mimics for the Evaluation of Endothelialization of Intravascular Devices," Tissue Eng, 12, 2006, pp. 3431-3438.
Chang et al., "Directed three-Dimensional Growth of Microvascular Cells and Isolated Microvessel Fragments," Cell Transplantation, 15, 2006, pp. 533-540.
Chrobak et al., "Formation of Perfused, Functional Microvascular Tubes in Vitro," Microvasc Res, 71, 2006, pp. 185-196.
Dahl et al., "Decellularized Native and Engineered Arterial Scaffolds for Transplantation," Cell Transplantation, 12, 2003, pp. 659-666.
Ferrara et al, "Vascular Endothelial Growth Factor is Essential for Corpus Luteum Angiogenesis," Nature Medicine, 4, 1998, pp. 336-340.
Folkman, J., "Angiogenesis: An Organizing Principle for Drug Discovery?," Nat Rev Drug Discov, 6, 2007, pp. 273-286.
Freed et al., "Advanced tools for tissue engineering: scaffolds, bioreactors, and signaling," Tissue Eng. 12(12), 2006, pp. 3285-3305.
Frerich et al., "Microvascular Engineering in Perfusion Culture: Immunohistochemistry and CLSM Findings," Head Face Med, 2:26, 2006.
Gonen-Wadmany et al., "Controlling the Cellular Organization of Tissue-Engineered Cardiac Constructs," Ann N Y Acad Sci, 1015, 2004, pp. 299.
Hoying et al., "Angiogenic Potential of Microvessel Fragments Established in Three-Dimensional Collagen Gels," In Vitro Cell Dev Biol Anim, 32, 1996, pp. 409-419.
Jain et al., "Engineering vascularized tissue," Nature Biotechnology, 23, 2005, pp. 821-823.
Jain, RK, "Molecular Regulation of Vessel Maturation," Nature Medicine, 9, 2003, pp. 685-693.

Jensen et al., "Inhibition of Hypoxia Inducible Factor-1alpha (HIF-1alpha) Decreases Vascular Endothelial Growth Factor (VEGF) Secretion and Tumor Growth in Malignant Gliomas," Journal of Neuro-oncology, 78, 2006, pp. 233-247.
Ko et al., "Engineering Thick Tissues—the Vascularisation Problem," European Cells & Materials, 14, 2007, pp. 1-18.
Koike et al., "Tissue Engineering: Creation of Long-Lasting Blood Vessels," Nature, 428, 2004, pp. 138-139.
Korin et al., "A Parametric Study of Human Fibroblasts Culture in a Microchannel Bioreactor," Lab Chip, 7(5), 2007, pp. 611-617.
Krishnan et al., "Effect of Mechanical Boundary Conditions on Orientation of Angiogenic Microvessels," Cardiovascular Research, 78, 2008, pp. 324-332.
Krishnan et al. "Interaction of Angiogenic Microvessels With the Extracellular Matrix," Am J Physiol Heart Circ Physiol, 293, 2007, pp. H3650-H3658.
Lanzen et al., "Direct Demonstration of Instabilities in Oxygen Concentrations Within the Extravascular Compartment of an Experimental Tumor," Cancer Research, 66, 2006, pp. 2219-2223.
Le Noble et al., "Flow Regulates Arterial-Venous Differentiation in the Chick Embryo Yolk Sac," Development (Cambridge, England), 131, 2004, pp. 361-375.
McFetridge et al., "Vascular Tissue Engineering: Bioreactor Design Considerations for Extended Culture of Primary Human Vascular Smooth Muscle Cells," Asaio J, 53, 2007, pp. 623-630.
Morsi et al., "Development of a Novel Pulsatile Bioreactor for Tissue Culture," J Artif Organs, 10, 2007, p. 109.
Neumann et al., "Tissue Engineering of Perfused Microvessels," Microvasc Res, 66, 2003, pp. 59.
Niklason et al., "Functional Arteries Grown in Vitro," Science, 284, 1999, pp. 489-493.
Pepper, MS, "Manipulating Angiogenesis. From Basic Science to the Bedside," Arterioscler Thromb Vasc Biol, 17, 1997, pp. 605-619.
Ramanujan et al., "Diffusion and Convection in Collagen Gels: Implications for Transport in the Tumor Interstitium," Biophysical Journal, 83, 2002, pp. 1650-1660.
Salzmann et al., "Inflammation and Neovascularization Associated With Clinically Used Vascular Prosthetic Materials," Cardiovasc Pathol, 8, 1999, pp. 63-71.
Secomb et al., "Information Transfer in Microvascular Networks," Microcirculation, 9, 2002, pp. 377-387.
Shepherd et al., "Rapid Perfusion and Network Remodeling in a Microvascular Construct After Implantation," Arterioscler Thromb Vasc Biol, 24, 2004, pp. 898-904.
Shepherd et al., "Microvascular Transplantation After Acute Myocardial Infarction," Tissue Engineering, 13:12, 2007, pp. 2871-2879.
Takei et al., "Fabrication of Endothelialized Tube in Collagen Gel as Starting Point for Self-Developing Capillary-Like Network to Construct Three-Dimensional Organs in Vitro," Biotechnol Bioeng, 95:1, 2006, pp. 1-7.
Teebken et al., "Tissue Engineering of Small Diameter Vascular Grafts," Eur J Vasc Endovasc Surg, 23, 2002, pp. 475-485.
Williams et al., "Endothelial Cell-Smooth Muscle Cell Co-Culture in a Perfusion Bioreactor System," Ann Biomed Eng, 33, 2005, p. 920.
Yamakawa et al., "Hypoxia-Inducible Factor-1 Mediates Activation of Cultured Vascular Endothelial Cells by Inducing Multiple Angiogenic Factors," Circulation Research, 93, 2003, pp. 664-673.
Yancopoulos et al., "Vascular-Specific Growth Factors and Blood Vessel Formation," Nature, 407, 2000, pp. 242-248.
Zilberberg et al., "Structure and Inhibitory Effects on Angiogenesis and Tumor Development of a New Vascular Endothelial Growth Inhibitor," J Biol Chem, 278, 2003, pp. 35564-35573.
ISA/US, International Search Report and Written Opinion for International Patent Application No. PCT/US09/57500, mailed Dec. 4, 2009.

* cited by examiner

FIG. 6A-1
| FIG. 6A | FIG. 6B |
|---|---|
| FIG. 6A-1 | FIG. 6B-1 |
| FIG. 6A-2 | FIG. 6B-2 |
| FIG. 6A-3 | FIG. 6B-3 |
FIG. 6B-1
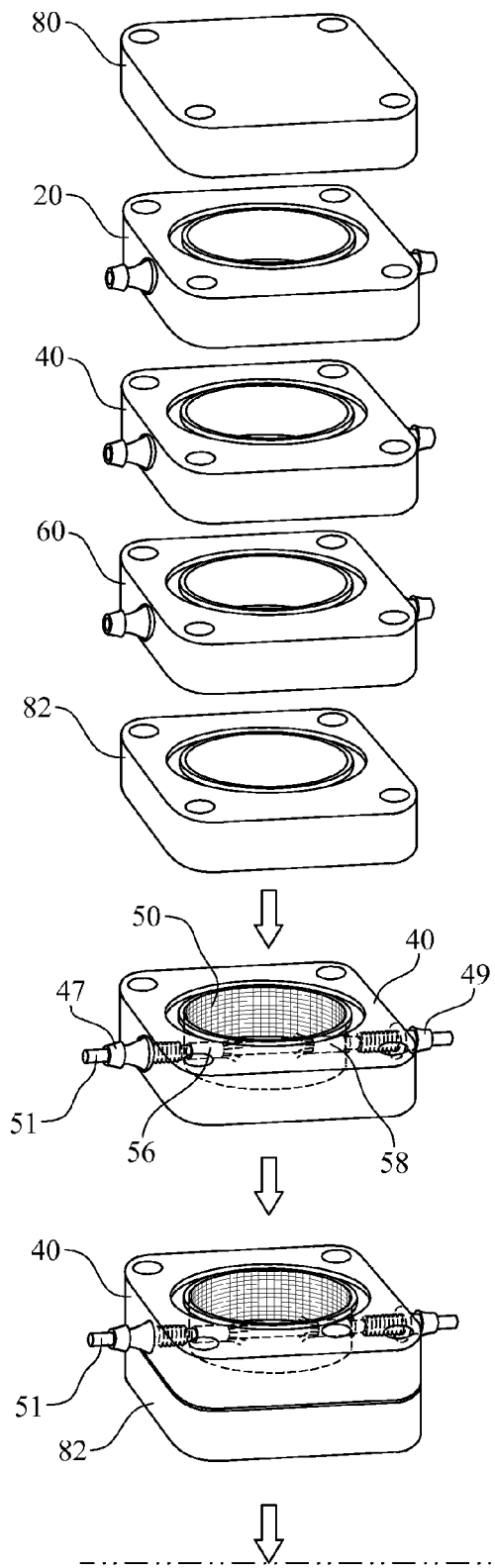
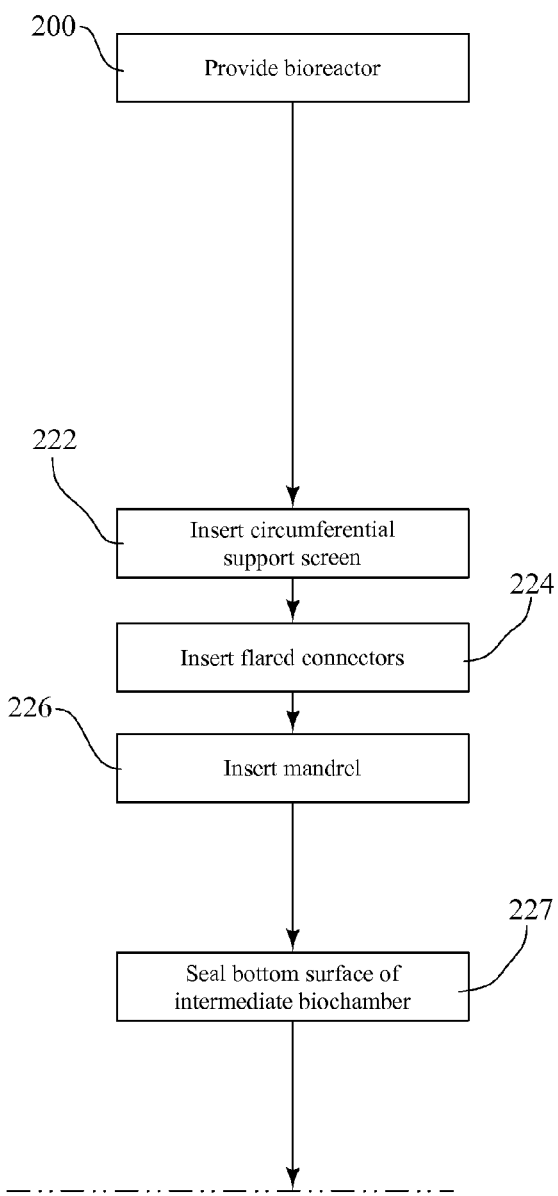

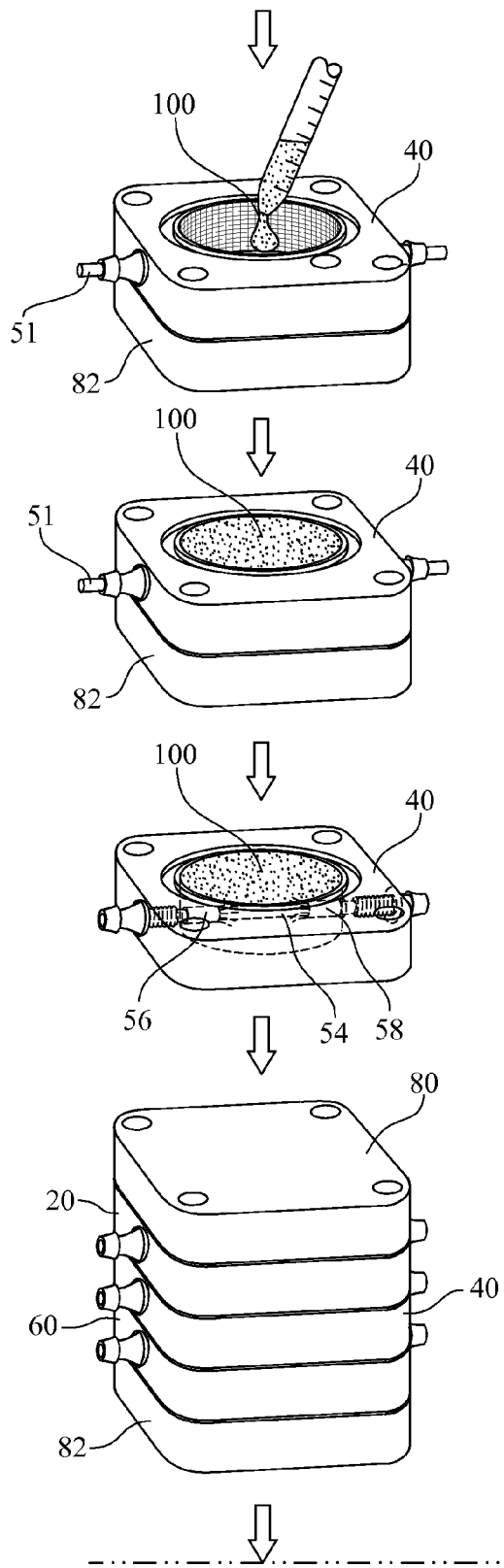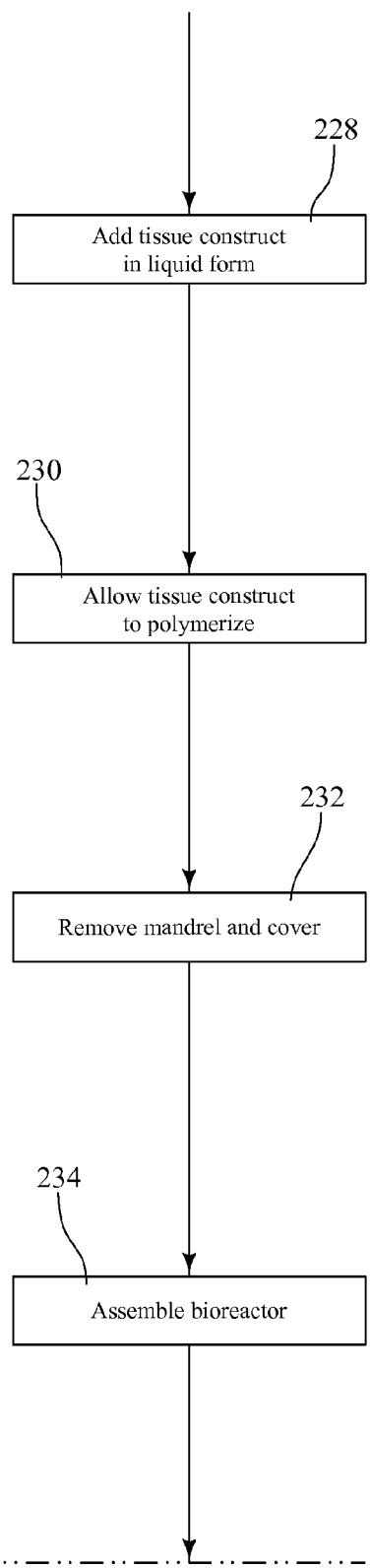

BIOREACTORS, SYSTEMS, AND METHODS FOR VASCULARIZING TISSUE CONSTRUCTS

RELATED APPLICATIONS

This application claims priority to U.S. Provisional Application Ser. No. 61/098,628, filed Sep. 19, 2008, and U.S. Provisional Application Ser. No. 61/221,153 filed Jun. 29, 2009, the entire disclosures of which are incorporated herein by this reference.

GOVERNMENT INTEREST

Subject matter described herein was made with U.S. Government support under Grant Number R01EB007556 awarded by the National Institutes of Health. The government has certain rights in the described subject matter.

TECHNICAL FIELD

The presently-disclosed subject matter relates to bioreactors, systems, and methods for vascularizing tissue constructs. In particular, the presently-disclosed subject matter relates to modular bioreactors capable of promoting the growth and development of a vascular network in a tissue construct.

BACKGROUND

There are a number of clinical situations where there is a need to re-establish or improve blood flow to a compromised or damaged tissue or organ. Often, the introduction of a new conduit vessel, either natural or artificial, upstream of an affected tissue or organ is sufficient to re-establish blood flow and relieve the symptoms exhibited by the affected tissue or organ. However, in situations where the replacement of an upstream, diseased conduit vessel does not resolve the condition, such as ischemia, it is necessary to regenerate the vascular supply within the tissue or organ. In these situations, the goal is thus to expand an existing vascular bed, especially the downstream vasculature, as a means to provide alternate and/or additional avenues for tissue or organ perfusion. In this regard, engineered tissue constructs offer promise to facilitate tissue healing and/or the replacement of compromised or damaged tissues and organs.

Current tissue engineering strategies, however, are hampered by the inability to pre-build a vasculature within the engineered construct. Indeed, the success of any tissue-engineered construct is highly dependent on the presence of a functional, invested vasculature within the construct as well as the ability to quickly perfuse the tissue construct once it is implanted into a subject. Any tissue construct greater in dimension than a few millimeters is too large for oxygen and nutrients to efficiently diffuse into the construct cells from the external environment and the surrounding host tissue. As such, the ability to grow and develop a vascular network within the construct is important for not only in vitro tissue construction, but also for in vivo vascular regeneration.

Existing strategies for building microvessels in vitro have involved a "de novo" approach in which freshly isolated or cultured vascular cells are placed within a scaffold, such as one formed by drilling channels into collagen sponges, by polymerizing collagen around metal or polymeric mandrels, or by utilizing polymer grafts. The vascular tubes that are formed by these microvascular constructs are capable of progressing into true microvessels and microvessel networks, but only when they are implanted into a living host. Alternative methods for building microvessels in vitro have employed isolated microvessel segments instead of cultured vascular cells, and have embedded these segments in a three-dimensional collagen matrix. In these later approaches, no further manipulation or addition of factors, such as growth factors or morphogens, is necessary to produce a new microvasculature network. However, the bioreactors that these three-dimensional constructs are produced within fail to provide sufficient perfusion paths through the constructs such that flow through the construct is maintained and the microvessels segments subsequently propagate into an organized and functional network of microvessels.

In any event, known methods and devices for building vessels in vitro are only capable of building microvessels within a preformed scaffold or are only capable of building a microvascular network that lacks organized perfusion paths within the construct itself. Furthermore, the known methods and devices for building vessels have only focused on building a collection of microvessels and have not sufficiently addressed how to build an organized network of microvessels such that a particular construct can then be implanted into an existing tissue and readily perfused, which is of great importance in treating compromised or damaged tissues or organs.

SUMMARY

This summary describes several embodiments of the presently-disclosed subject matter, and, in many cases, lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes bioreactors, systems, and methods for vascularizing a tissue construct.

In some embodiments, a modular bioreactor is provided that includes an upper biochamber; a lower biochamber; and an intermediate biochamber that is positioned between the upper biochamber and the lower biochamber, where each biochamber further includes an interior wall, which defines a centrally-disposed cavity, as well as an inflow port and an outflow port that is in fluid communication with each centrally disposed cavity. Upon assembly of the upper biochamber, intermediate biochamber, and lower biochamber, the centrally-disposed cavities of each biochamber are aligned such that each biochamber is in fluid communication with each other biochamber of the bioreactor.

In some embodiments, an exemplary bioreactor further comprises an upper cover and a lower cover that can be positioned onto the upper biochamber and lower biochamber, respectively, such that the bioreactor is closed on both ends.

In some embodiments, a support screen can be positioned in the centrally-disposed cavity of the intermediate biochamber to allow a matrix, such as a collagen matrix, to be inserted into the centrally-disposed cavity of the intermediate biochamber, engage the support screen, and provide a substrate for various cells and cellular structures.

With regard to the matrix of the presently-disclosed bioreactors, in some embodiments, the matrix defines a conduit that extends through the matrix and is in fluid communication with the inflow port and the outflow port of the intermediate biochamber. In some embodiments, a first connector is positioned within the centrally-disposed cavity and aligned with the inflow port and the conduit defined through the matrix. In some embodiments, a second connector is further positioned within the centrally-disposed cavity of the intermediate biochamber and is aligned with the outflow port and the conduit defined through the matrix. In some embodiments, the first connector or both the first connector and the second connector are flared connectors such that the flared portion of the connector extends into the centrally-disposed cavity of the intermediate biochamber and into the matrix.

In some embodiments of the presently-disclosed bioreactors, one or more spacers, each having a centrally-disposed cavity, are incorporated into an exemplary bioreactor such that the centrally-disposed cavity of each spacer is in fluid communication with the centrally-disposed cavity of one or more adjacent biochambers. In some embodiments, the one or more spacers can be positioned between two biochambers. In other embodiments, the one or more spacers can be positioned between the upper biochamber and the upper cover, the lower biochamber and the lower cover, or both.

Further provided, in some embodiments of the presently-disclosed subject matter, are systems for vascularizing a tissue construct. In some embodiments, a system is provided that comprises: a bioreactor having an upper biochamber, a lower biochamber, and an intermediate biochamber positioned between the upper biochamber and lower biochamber, where each biochamber has a centrally-disposed cavity; a tissue construct positioned within the cavity of the intermediate biochamber; and a means for perfusing the bioreactor with a cell culture media such that the tissue construct undergoes vascularization. In some embodiments, the means for perfusing the bioreactor with the cell culture media includes a pump, along with an inflow port and an outflow port that are positioned in each bio chamber such that the ports are in fluid communication with the centrally-disposed cavity of each biochamber.

Still further provided, in some embodiments of the presently-disclosed subject matter, are methods for vascularizing a tissue construct. In one exemplary implementation, a bioreactor, having an upper biochamber, a lower biochamber, and an intermediate biochamber positioned between the upper biochamber and the lower biochamber, is initially provided. Each biochamber includes a centrally-disposed cavity, with the cavities of each biochamber in fluid communication with each other. Then, a tissue construct, such as tissue construct comprised of a microvascular fragment incorporated into a matrix, is positioned within the cavity of the intermediate biochamber. The upper biochamber and the lower biochamber are then perfused with a cell culture media such that the tissue construct is indirectly perfused and undergoes vascularization. In some embodiments, the biochambers are perfused with a cell culture media by using an inflow port and an outflow port that are included in each biochamber and are in fluid communication with the centrally disposed cavity of each biochamber.

With respect to the positioning of the tissue construct within the cavity of the intermediate biochamber, in some embodiments, the positioning of the tissue construct is performed by first positioning a support screen in the centrally-disposed cavity of the intermediate biochamber. One or more connectors, such as flared connectors, are then inserted within the centrally-disposed cavity of the intermediate biochamber and aligned with the inflow port, the outflow port, or both the inflow and the outflow port of the intermediate biochamber. After the connectors are inserted, a mandrel is inserted through the inflow port and the outflow port of the intermediate biochamber such that the mandrel extends through the one or more connectors, the support screen, and the centrally-disposed cavity of the intermediate biochamber. At that point, an unformed tissue construct is then added to the centrally-disposed cavity of the intermediate biochamber and allowed to polymerize into a three-dimensional construct. Once the construct has sufficiently polymerized, the mandrel can then be removed from the construct to provide a tissue construct that includes a conduit, which extends through the tissue construct and is in flow communication with the inflow port and the outflow port of the intermediate biochamber. In some embodiments, the conduit can then be lined with a plurality of endothelial cells or vascular cell precursors.

By providing a tissue construct with a conduit that extends through the construct and is in fluid communication with the inflow port and the outflow port of the intermediate biochamber, in some embodiments, the intermediate biochamber can further be perfused for a period of time such that the tissue construct is directly perfused in order to maintain the viability of and to mature the vessels within the construct.

Advantages of the presently-disclosed subject matter will become evident to those of ordinary skill in the art after a study of the description, Figures, and non-limiting Examples in this document.

DESCRIPTION OF THE DRAWINGS

FIG. 7A is a graph depicting the density of microvessels in a section of the microvascular construct where the percent of cells staining positive for the endothelial cell marker GS1 (y-axis), per $mm^2$, is plotted against the different perfusion schemes (x-axis). FIGS. 7B and 7C are graphs depicting the percent of microvessels with lumens within GS1-stained sections (FIG.

Figure 7A:
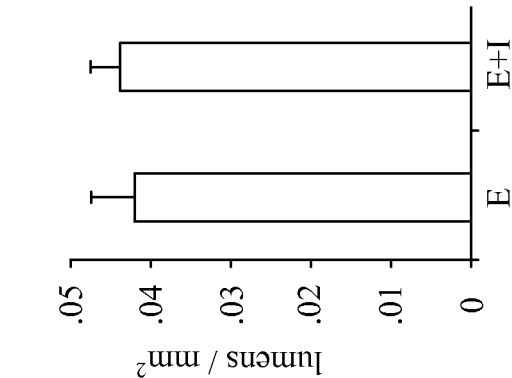
FIGS. 7A-7C are various graphs depicting the density of vessels and the percentage of vessels with lumens in microvascular constructs subsequent to indirect perfusion of the constructs by perfusing cell culture media through the upper and lower biochambers (E) or subsequent to direct perfusion of the constructs by also perfusing cell culture media through the intermediate biochamber (E+I).
Figure 7B:
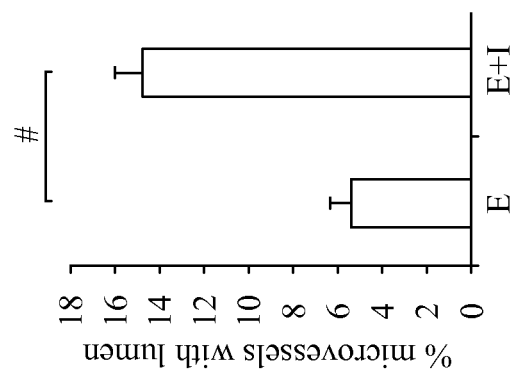
Figure 7C:
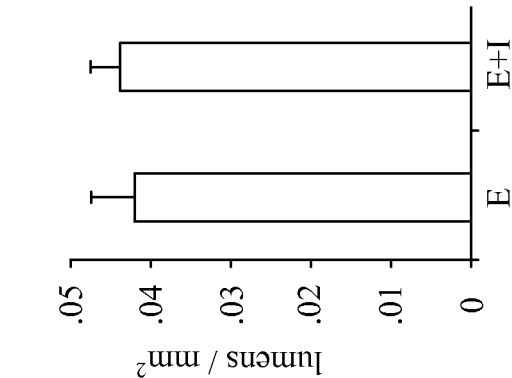

7B) and depicting the number of lumens per mm² when the lumen numbers are normalized to construct cross section (FIG. 7C).

Figure 8A:
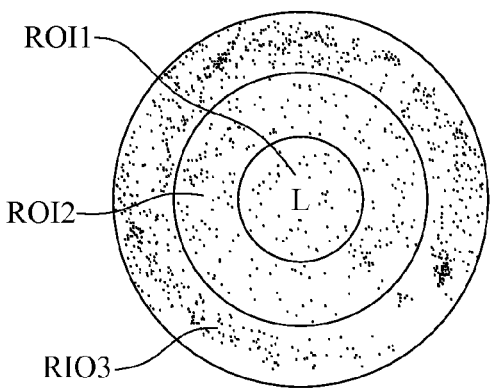
Figure 8B:
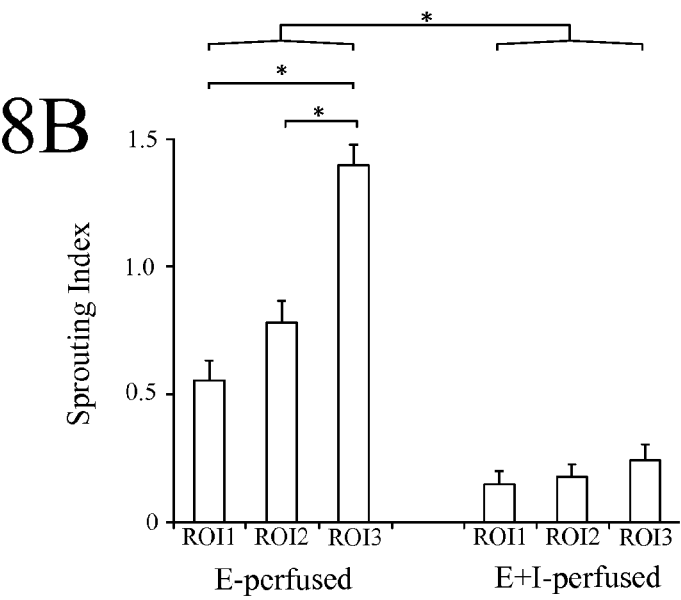
Figure 8C:
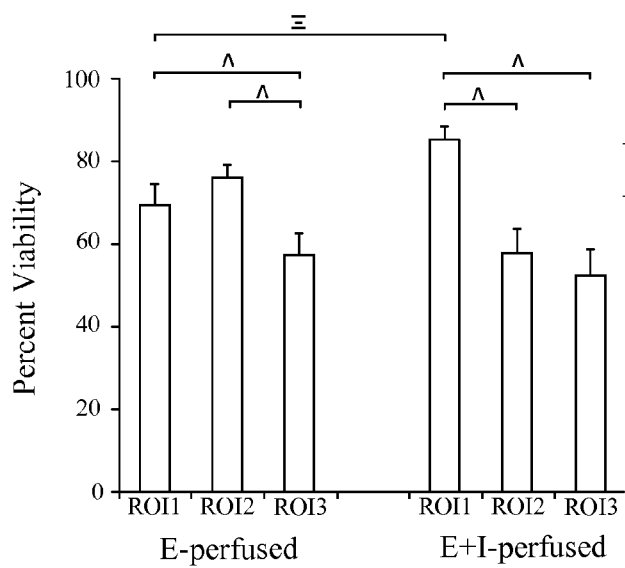

FIGS. 8A-8C are an illustration and graphs depicting three regions of interest (ROI 1-3) in a cross-section of an exemplary microvascular construct perfused with either the E perfusion scheme or the E+I perfusion scheme. FIG. 8A is an illustration depicting the three ROI and showing the microvessels within the various regions, with "L" indicating the lumen or conduit extending through the construct. FIGS. 8B and 8C are graphs depicting the extent of sprouting (FIG. 8B) and the viability of microvessel fragments (FIG. 8C) within the various ROI in the different perfusion schemes.

Figure 9:
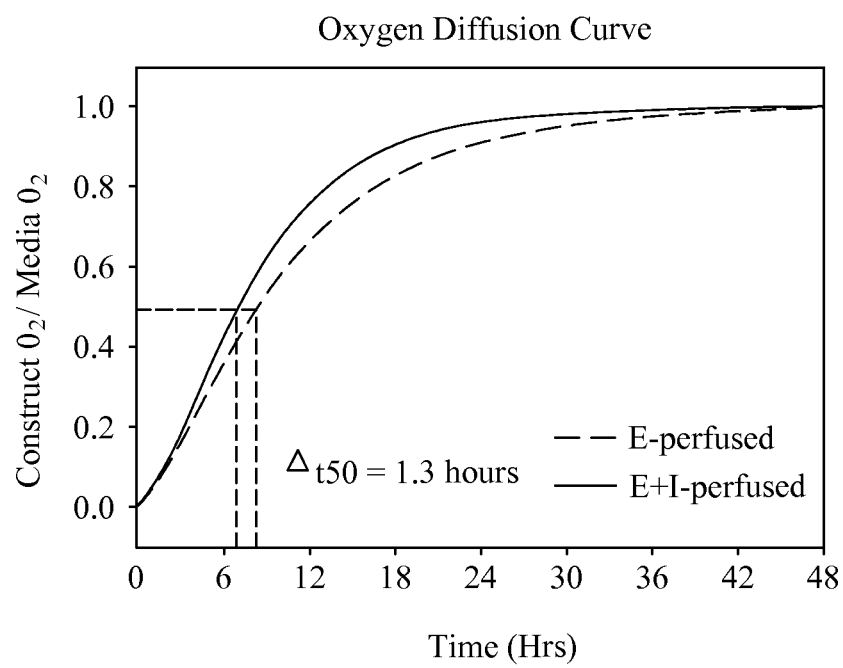

FIG. 9 is a graph of an oxygen diffusion curve depicting the equilibration of microvascular constructs to media oxygen levels in the E perfusion scheme and in the E+I perfusion scheme.

Figure 10:
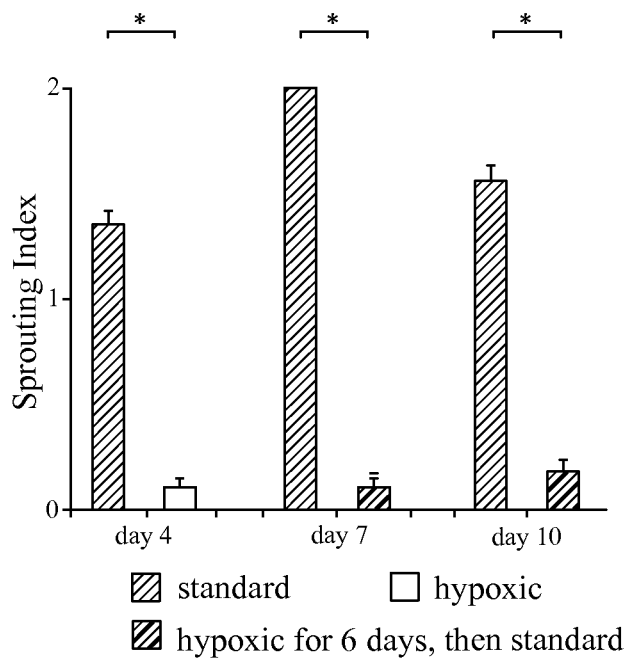

FIG. 10 is a graph depicting the extent of sprouting in microvascular constructs under hypoxic conditions at various time points.

Figure 11:
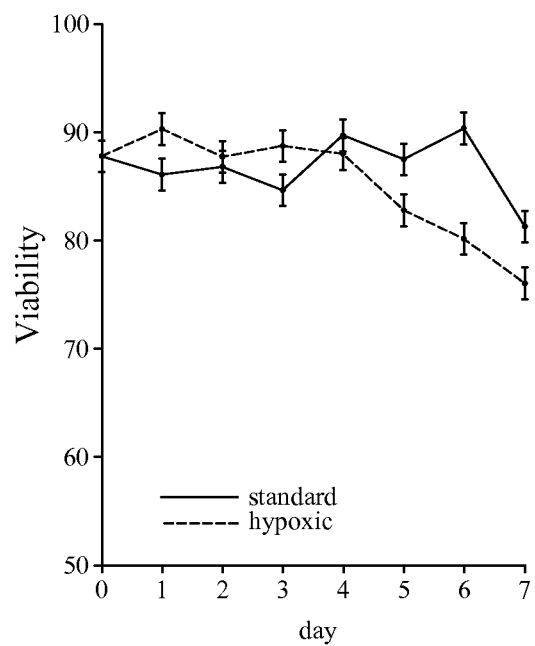

FIG. 11 is a graph depicting the viability of microvascular fragments under hypoxic conditions at various time points.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

The presently-disclosed subject matter includes bioreactors, systems, and methods for vascularizing tissue constructs.

The vasculature is a dynamic network of various caliber blood vessels that plays an integral role in maintaining homeostasis. In addition to providing nutrient delivery and metabolic waste removal, the vasculature acts as a conduit for the local and systemic distribution of cell signals. In vivo, vascular beds also have the capacity to adapt to the changing needs of the surrounding tissue. In common physiological processes and in response to acute and chronic diseases, existing vasculatures can be triggered to form new vessels, i.e., undergo angiogenesis. These neovessels extend out into the surrounding matrix, inosculating with other sprouts and newly formed vessels. Over time, these nascent vessels become fully integrated into a vascular network capable of providing increased perfusion that is tailored to the needs of the surrounding tissue.

To that end, the presently-disclosed subject matter includes bioreactors, systems, and methods for vascularizing tissue constructs in vitro that can then be implanted in vivo and form a new vasculature that is contiguous with the existing vasculature of a host (i.e., a human or animal subject). In some embodiments of the presently-disclosed subject matter, a bioreactor is used to recapitulate in vivo angiogenic behavior and develop a vascularized tissue construct. In certain embodiments, small caliber blood vessels (e.g., arterioles, capillaries, and venules) are isolated from rat epididymal fat and suspended within collagen matrices. Once placed in an exemplary bioreactor, these microvessels retain their normal three-dimensional architecture and spontaneously form endothelial sprouts (i.e., angiogenesis) without the addition of exogenous angiogenic factors. Furthermore, within 7 days, the endothelial sprouts grow out into the matrix to form neovessels which inosculate with other nascent microvessels and yield complex three-dimensional networks of microvessels, such as what is observed in a viable microvascular bed of a subject.

Figure 1:
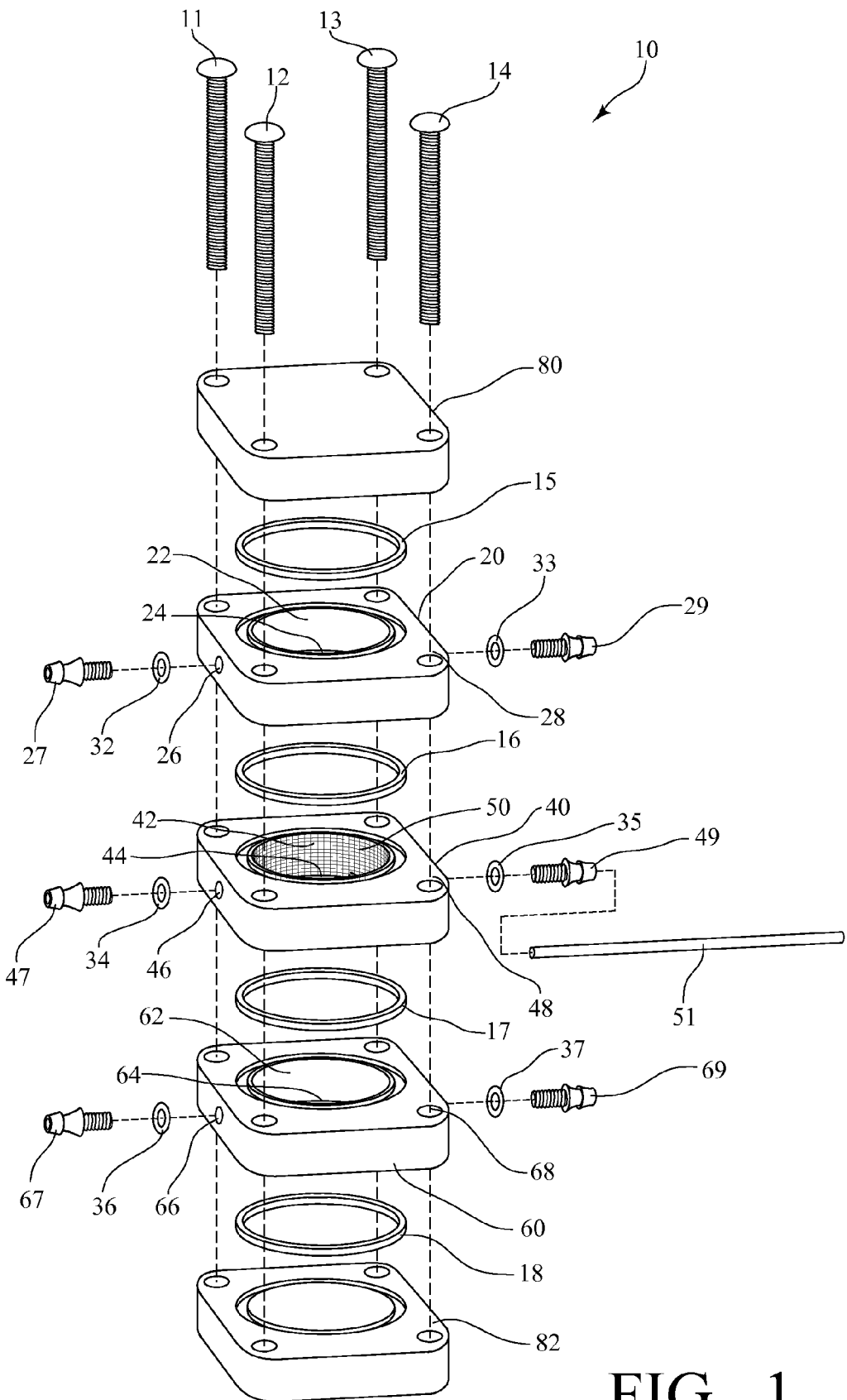
FIG. 1 is an exploded view of an exemplary bioreactor in accordance with the presently-disclosed subject matter, which includes an upper biochamber, a lower biochamber and an intermediate biochamber positioned between the upper biochamber and the lower biochamber.

Referring first to FIG. 1, an exemplary bioreactor 10 of the presently-disclosed subject matter includes an upper biochamber 20; a lower biochamber 60; and an intermediate biochamber 40 that is positioned between the upper biochamber 20 and the lower biochamber 60. Each biochamber 20,40,60 has an interior wall 22,42,62 that defines a centrally-disposed cavity 24,44,64 such that, in an assembled form, the centrally-disposed cavities 24,44,64 of each biochamber 20,40,60 are aligned and in fluid communication with each other. In the exemplary embodiment of FIG. 1, each biochamber 20,40,60 is a substantially square module that is about 10 mm in height, about 39.5 mm in width, and about 39.5 mm in length, with a centrally-disposed cavity that is about 17 mm in diameter. Of course, to the extent is may be desired, the foregoing dimensions can be increased or decreased to fit the needs of a particular application. Furthermore, it is also contemplated that multiple cavities can be incorporated in an exemplary biochamber without departing from the spirit and scope of the subject matter disclosed herein, such that an exemplary biochamber can be provided that includes two or more discrete cavities within each biochamber.

In the exemplary bioreactor 10 depicted in FIG. 1, each biochamber further includes an inflow port 26,46,66 and an outflow port 28,48,68 that are in fluid communication with the centrally-disposed cavities 24,44,64 of each biochamber 20,40,60. As depicted in FIG. 1, in some embodiments, the inflow port 26,46,66 and the outflow port 28,48,68 of each biochamber 20,40,60 are positioned on opposite sides of each biochamber 20,40,60 such that fluid flowing through an exemplary biochamber 20,40,60 flows from one side of the biochamber 20,40,60 to an opposite side of the biochamber 20,40,60 or, in some embodiments, flows in a linear path through a tissue construct, as described further below. It is further contemplated, however, that in order to incorporate different flow paths through an exemplary bioreactor or a particular tissue construct, the particular arrangement of the inflow port 26,46,66 and the outflow port 28,48,68 can, of course, be varied without departing from the spirit and scope of the subject matter disclosed herein. Furthermore, it is also contemplated that multiple (e.g., two or more) inflow ports 26,46,66 and outflow ports 28,48,68 can be incorporated into an exemplary bioreactor such that an exemplary bioreactor can be provided that includes multiple inputs, multiple outputs, or both from exemplary biochambers and their respective cavities.

Referring still to FIG. 1, the exemplary bioreactor 10 further includes an upper cover 80 and a lower cover 82 that are positioned on and secured to a top surface of the upper biochamber 20 and a bottom surface of the lower biochamber 60, respectively, such that an exemplary bioreactor 10 is provided as a substantially closed system with the only input into the bioreactor 10 and output from the bioreactor 10 coming from the inflow ports 26,46,66 and the outflow ports 28,48,68, respectively. Alternatively, in some embodiments, the top surface of the upper biochamber 20 and the bottom surface of lower biochamber 60 can form a closed top surface and closed bottom surface of an exemplary bioreactor (not shown), such that, upon assembly of the biochambers 20,40,60, the bioreactor forms a substantially closed system without the use of any separate covers.

The exemplary bioreactor 10 depicted in FIG. 1 is typically assembled by stacking the biochambers 20,40,60 and the upper and lower covers 80,82, and then securing the biochambers 20,40,60 and the covers 80,82 to one another. As depicted in FIG. 1, in some embodiments, the biochambers 20,40,60 are secured to one another by inserting a series of bolts 11,12,13,14 through holes located in each corner of the biochambers 20,40,60 and associated covers 80,82. To prevent fluid, such as cell culture media, from later leaking out of the bioreactor 10, in some embodiments, a series of gaskets or o-rings 15,16,17,18 can be placed in recesses formed around the centrally-disposed cavities 24,44,64 of each biochamber 20,40,60 before the bolting the bioreactor 10 together.

With further respect to the assembly of an exemplary bioreactor 10, and referring still to FIG. 1, the exemplary bioreactor 10 can further include a number of adapters 27,29,47,49,67,69. During assembly, the adapters 27,29,47,49,67,69 are inserted into the inflow ports 26,46,66 and the outflow ports 28,48,68 of the biochambers 20,40,60 and provide a means for attaching and placing the biochambers 20,40,60 of an exemplary bioreactor 10 in-line with a perfusion system. As depicted in FIG. 1, in some embodiments, the adapters 27,29,47,49,67,69 contain threaded portions that allow them to be secured into the inflow ports 26,46,66 and the outflow ports 28,48,68 along with gaskets 32,33,34,35,36,37, which surround the adapters and prevent leaks from occurring around the inflow ports 26,46,66 and the outflow ports 28,48,68. Once the adapters 27,29,47,49,67,69 and associated gaskets 32,33,34,35,36,37 are secured to the inflow ports 26,46,66 and the outflow ports 28,48,68 of the biochambers 20,40,60, lines can then be connected to adapters 27,29,47,49,67,69 and to a perfusion system, such as one including a peristaltic or other suitable pump, so that each biochamber 20,40,60 can be selectively perfused with a cell culture media. In some embodiments, the lines connecting an exemplary bioreactor 10 to a perfusion system are gas permeable lines that include in-line T-connectors such that direct access is provided to the perfusion circuit and, subsequently, to the biochambers 20,40,60 and their associated components.

Figure 3:
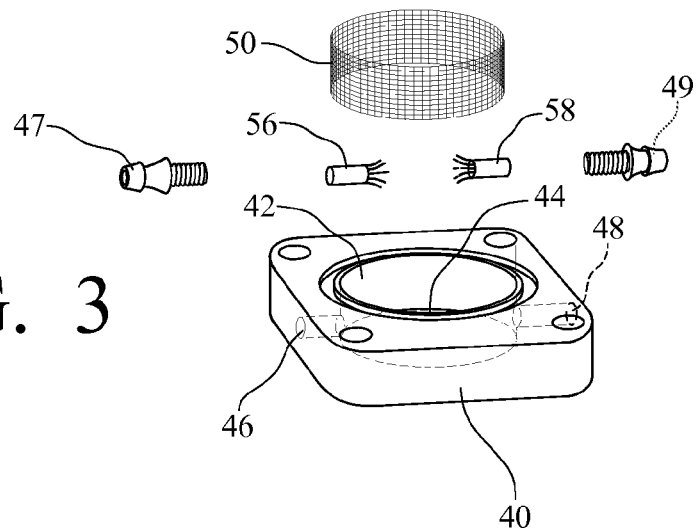
FIG. 3 is an exploded view of the intermediate biochamber of the exemplary bioreactor depicted in FIG. 1, and further illustrating an exemplary support screen and flared connectors.
Figure 4:
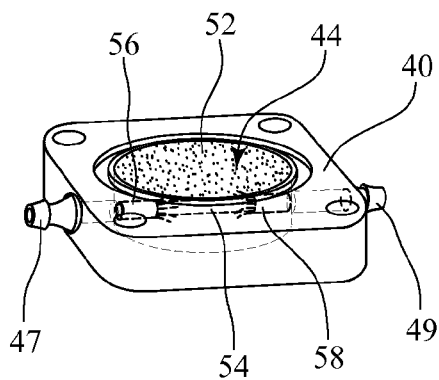
FIG. 4 is a perspective view of the intermediate biochamber depicted in FIG. 3, but showing the intermediate biochamber in an assembled form and further illustrating a matrix positioned within the centrally-disposed cavity.

Referring now to FIGS. 3 and 4, in some embodiments of the presently-disclosed subject matter, various components are positioned within the intermediate biochamber 40 to assist in the development of a tissue construct. For example, in some embodiments, and as depicted in FIGS. 3 and 4, a support screen 50 is positioned in the centrally-disposed cavity 44 of the intermediate biochamber 40. The support screen 50 can be made of any material that can be suitably engaged by a matrix or a tissue construct, as is described in further detail below. As will be recognized by those of ordinary skill in the art, a number of different materials can be used to form such a support screen including, but not limited to: polyamides (e.g., nylon), polyesters (e.g., DACRON™), polystyrene, polypropylene, polyacrylates, polyvinyl compounds, polycarbonates, polytetrafluoroethylene; cotton, polyglycolic acid, cat gut sutures, cellulose, dextran, gelatin, metals, ceramics, glass-ceramics, composite materials, drug eluting stent materials, memory alloys, physically or chemically surface-modified metals or ceramics (e.g., micro- or nano-patterned), glass, bioglass, or biologically-coated metal, ceramic, composite, or polymeric materials. Any of these materials can be used to form a support screen and provide a structure that can be engaged by a matrix or a tissue construct. In some embodiments, the support screen is a 500 mesh nylon screen that forms a circumferential support screen 50 around the centrally-disposed cavity 44 of the intermediate biochamber 40.

With further respect to an exemplary intermediate biochamber 40, and referring still to FIG. 4, in some embodiments, a matrix 52 is positioned within the centrally-disposed cavity of the intermediate biochamber 40 such that the matrix engages the support screen 50 and provides a substrate for cells. A suitable matrix 52 can be formed from any biocompatible material that is a gel, a semi-solid, or a solid at room temperature (e.g., 25° C.) and can be used as a three-dimensional substrate for cells or tissues. Exemplary materials that can be used to form a matrix in accordance with the presently-disclosed subject matter include, but are not limited to polymers and hydrogels comprising collagen, fibrin, chitosan, MATRIGEL™, polyethylene glycol, dextrans including chemically crosslinkable or photo-crosslinkable dextrans, and the like, as well as electrospun biological, synthetic, or biological-synthetic blends. In some embodiments, the matrix is comprised of collagen.

As depicted in FIG. 4, in some embodiments, the matrix 52 is substantially cylindrical and fills the centrally-disposed cavity 44 of the intermediate biochamber. In some embodiments, the matrix 52 defines a conduit 54 that extends through the matrix 52 and is in fluid communication with the inflow port 46 and the outflow port 48 of the intermediate biochamber 40. By including a conduit that extends through the matrix 52, when fluid, such as cell culture media, is perfused through the exemplary bioreactor depicted in FIGS. 1 and 2, the fluid is able to not only enter the upper biochamber 20 and the lower biochamber 40, but can also be perfused through the conduit 54 formed in the matrix 52 in the intermediate biochamber 40 such that fluid is perfused directly through the matrix 52.

Referring still to FIGS. 3 and 4, in some embodiments, a first connector 56 is positioned within the centrally-disposed cavity 44 of the intermediate biochamber 40 and aligned with the inflow port 46 and the conduit that is defined through the matrix 52. In some embodiments, a second connector 58 is further positioned within the centrally-disposed cavity 44 of the intermediate biochamber 40 and aligned with outflow port 48 and the conduit 54 that is defined through the matrix 52. In some embodiments, the first connector 56 or the first connector 56 and the second connector 58 are flared connectors such that the end of the connector that extends into the conduit 54 is flared and engages the portions of the matrix 52 surrounding the conduit 54. In some embodiments, in order to allow a greater interaction between the connectors and the surrounding matrix, an exemplary connector 56 or 58 is comprised of a porous or mesh-like material.

Figure 2:
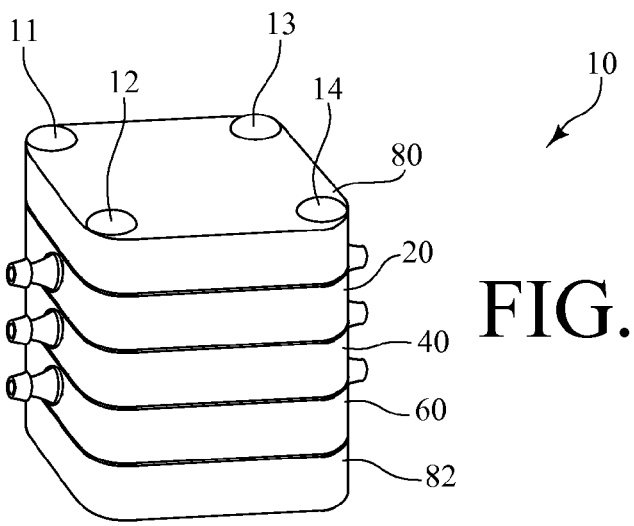
FIG. 2 is a perspective view of the exemplary bioreactor depicted in FIG. 1, but showing the bioreactor in an assembled form.

By providing one or more connectors 56,58 in the centrally-disposed cavity 44 of the intermediate biochamber 40 and aligning the connectors 56,58 with the conduit defined through the matrix 52, the connectors 56,58 provide a means to reduce the amount of longitudinal compression of the conduit 54 that may be observed when the exemplary bioreactor 10 of FIGS. 1 and 2 is perfused. Furthermore, in some embodiments, the inclusion of the connectors 56,58 allows the matrix 52 and its associated cells and tissues to be removed from the intermediate biochamber 40 and placed in a different culturing environment while retaining the patency of the conduit 54 or, alternatively, allows the matrix 52 and its associated components to be removed from the intermediate biochamber 40 and sutured into an existing vessel of a host, as described in more detail below.

Figure 5:
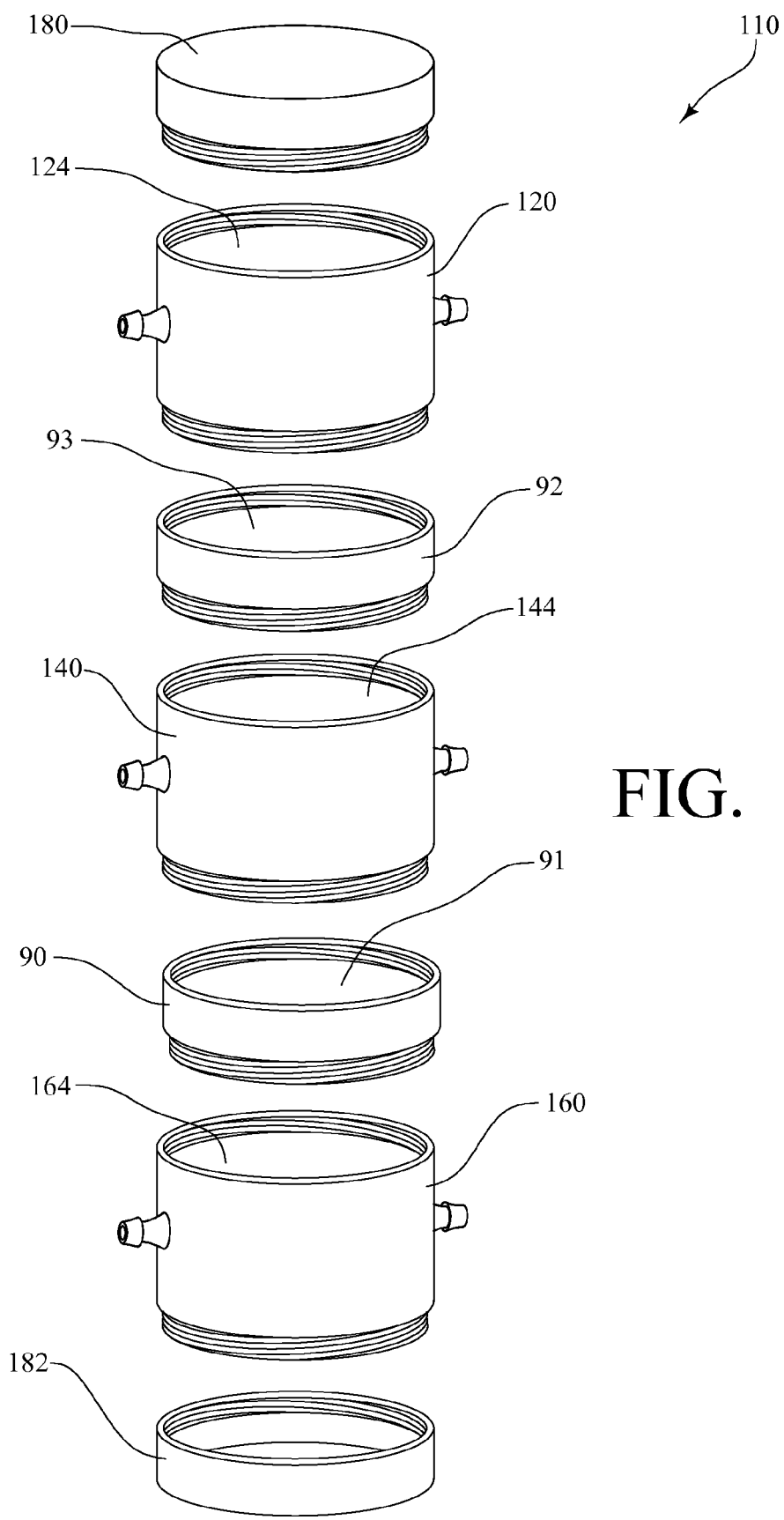
FIG. 5 is an exploded view of another exemplary bioreactor in accordance with the presently-disclosed subject matter, which includes two spacers positioned between the biochambers.

Referring now to FIG. 5, in some embodiments, an alternative bioreactor 110 is provided that comprises one or more spacers 90,92, which include a centrally-disposed cavity 91,93, similar to those found in the exemplary biochambers 20,40,60 depicted in FIG. 1. In that regard, the one or more spacers 90,92 can be positioned between biochambers 120, 140,160, as depicted in FIG. 5, such that the centrally-disposed cavities 91,93 of the spacers 90,92 are in fluid communication with the centrally-disposed cavities 124,144,164 of the biochambers 120,140,160. In other embodiments, the spacers 90,92 can be positioned between the upper biochamber 120 and an upper cover 180, between the lower biochamber 160 and a lower cover 182, or both. Regardless of the particular arrangement of exemplary spacers 90,92 in an exemplary bioreactor 110, however, the incorporation of one or more spacers 90,92 into an exemplary bioreactor 110 allows the internal volume of the bioreactor 10 to be expanded and thus permits the amounts of the fluid (e.g., cell culture media) and or the size of a tissue construct within an exemplary bioreactor 10 to be modulated, to the extent doing so may be desirable for a particular application. Furthermore, the incorporation of spacers within an exemplary bioreactor is, of course, not limited to the exemplary bioreactor 110 depicted in FIG. 5. One or more spacers can also be incorporated into the exemplary bioreactor 10 depicted in FIGS. 1 and 2, or other embodiments of the presently-disclosed bioreactors, without departing from the spirit and scope of the subject matter disclosed herein.

As a further refinement, and referring still to FIG. 5, an exemplary bioreactor 110 can also be directly assembled, without the use of gaskets or bolts, by including threaded portions on the biochambers 120,140,160, the covers 180, 182, and the spacers 90,92 (if utilized) such that the threaded portion of one component can be received by a corresponding threaded portion of an adjacent component and the bioreactor 110 can simply be screwed together.

An exemplary bioreactor of the presently-disclosed subject matter is designed to allow for simple aseptic assembly of its associated components and prevent the contamination of any tissue constructs that are subsequently developed within the bioreactor. As such, and referring to the exemplary bioreactors depicted in FIGS. 1 and 5, the biochambers (20,40,60 or 120,140,160), the upper covers (80 or 180), the lower covers (82 or 182), and the spacers (90,92) of an exemplary bioreactor (10 or 110) are usually fabricated from a biocompatible polymer, such as poly(carbonate), poly (methyl methacrylate), poly(sulfone), or the like, which are compatible with simple steam or gas sterilization techniques. As a further refinement, however, it is also contemplated that alternate polymer systems could be used to fabricate an exemplary bioreactor and sterilized by gamma irradiation techniques, or that ceramics, glass-ceramics, glass, and composite materials could be used to fabricate an exemplary bioreactor and sterilized with ethylene oxide, autoclave, ultraviolet radiation, or chlorine dioxide techniques.

Further provided, in some embodiments of the presently-disclosed subject matter, are systems and methods for vascularizing a tissue construct. The terms "vascularize," "vascularizing," or "vascularization" are used herein to refer to revising an existing vascular network or establishing a new functional or substantially functional vascular network. As such, the terms vascularize, vascularizing, or vascularization include, but are not limited to, the formation of new vessels (i.e., angiogenesis), the formation of a precursor vessel network, and the inosculation of the new vessels with other nascent vessels or with existing vessels to form a functional or substantially functional vascular network. A functional or substantially functional vascular network is one that perfuses or is capable of perfusing a tissue or organ to meet some or all of that tissue's or organ's nutritional, oxygen, and waste product elimination needs.

In some embodiments, the tissue constructs that are utilized in conjunction with the presently-disclosed systems and methods for vascularizing a tissue construct comprise a vascular fragment incorporated into a matrix, such as a three-dimensional collagen matrix. The term "vascular fragment" or "vessel fragment" is used herein to refer to a segment or piece of vascular tissue, including at least a part or segment of at least an artery, arteriole, capillary, venule, vein, or a combination thereof. As such, the terms vascular fragment or vessel fragment are further inclusive of the terms "microvessel fragment" or "microvascular fragment," which are used interchangeably herein to refer to a segment or piece of a smaller caliber vascular tissue, such as arterioles, capillaries, and venules. Typically, a vessel or microvessel includes endothelial cells arranged in a tube surrounded by one or more layers of mural cells, such as smooth muscle cells or pericytes, and can further comprise extracellular matrix components, such as basement membrane proteins. In some embodiments, the vascular fragments are obtained from vascular tissue, such as that found in skin, skeletal muscle, cardiac muscle, the atrial appendage of the heart, lung, mesentery, or adipose tissue. In some embodiments, the vascular fragments are adipose tissue microvessel fragments that can be obtained from various adipose tissues including, but not limited to, subcutaneous fat, perirenal fat, pericardial fat, omental fat, breast fat, epididymal fat, properitoneal fat, and the like.

The term "tissue construct" or "prevascularized tissue construct" or "engineered tissue construct" are used interchangeably herein to refer to a composition comprising at least one vascular fragment incorporated into a matrix, as defined herein. As noted, in some embodiments of the presently-disclosed subject matter, the tissue construct comprises a three-dimensional matrix, such as a collagen matrix, that incorporates at least one microvascular fragment. As such, in describing these embodiments, the term tissue construct can be used interchangeably with the term "microvascular construct."

In certain embodiments, the tissue constructs are prepared by first isolating one or more microvascular fragments from epididymal fat and then combining the microvascular fragments with a liquid, unpolymerized matrix material, such as cold, unpolymerized collagen, fibrin, or other nonpolymerized matrix materials, or the like. Once the microvascular fragments and non-polymerized matrix material have been combined, the unpolymerized construct can then be placed into a suitable vessel, such as the exemplary biochambers described above with reference to FIGS. 1-5, and allowed to polymerize into a three-dimensional construct.

One of ordinary skill in the art will understand that tissue constructs in a non-polymerized form, which are subsequently allowed to polymerize or gel, are capable of assuming a multitude of shapes. Thus, in certain embodiments, the ultimate size and shape of the polymerized construct depends, in part, on the size and shape of the vessel in which the construct is polymerized. For example, cylindrical or tubular constructs can be prepared by placing the unpolymerized vascular construct into a cylindrical centrally-disposed cavity of the exemplary intermediate biochamber described above with reference to FIGS. 1-5. Of course, to the extent it may be desired, different sizes or shapes of tissue constructs can be provided by altering the geometry of the centrally-disposed cavity of the exemplary biochamber, or other vessel, into which the unpolymerized construct is placed. Additionally, in certain embodiments, polymerized prevascularized constructs can be cut or trimmed into a desired size or shape. Thus, prevascularized constructs can be prepared in virtually any size and shape.

In certain embodiments, the tissue construct further comprises appropriate stromal cells, stem cells, Relevant Cells, or combinations thereof such that the tissue construct can be vascularized in an exemplary bioreactor, such as those described herein with reference to FIGS. 1-5, and then used to repair or replace a damaged tissue or organ. As used herein, the term "stem cells" refers broadly to traditional stem cells, progenitor cells, preprogenitor cells, precursor cells, reserve cells, and the like. Exemplary stem cells include, but are not limited to, embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including methods for isolating and culturing them, may be found in, among other places, Embryonic Stem Cells, Methods and Protocols, Turksen, ed., Humana Press, 2002; Weisman et al., Annu Rev. Cell. Dev. Biol. 17:387-403; Pittinger et al., Science, 284:143-47, 1999; Animal Cell Culture, Masters, ed., Oxford University Press, 2000; Jackson et al., PNAS 96(25):14482-86, 1999; Zuk et al., Tissue Engineering, 7:211-228, 2001; and U.S. Pat. Nos. 5,559,022, 5,672, 346 and 5,827,735. Descriptions of stromal cells, including methods for isolating them, may be found in, among other places, Prockop, Science, 276:71-74, 1997; Theise et al., Hepatology, 31:235-40, 2000; Current Protocols in Cell Biology, Bonifacino et al., eds., John Wiley & Sons, 2000; and U.S. Pat. No. 4,963,489. One of ordinary skill in the art will understand that the stem cells and/or stromal cells that are selected for inclusion in a tissue construct are typically selected when such cells are appropriate for the intended use of a particular construct.

The term "Relevant Cells," as used herein refers to cells that are appropriate for incorporation into a tissue construct, based on the intended use of that construct. For example, Relevant Cells that are appropriate for the repair, restructuring, or repopulation of particular damaged tissue or organ will typically include cells that are commonly found in that tissue or organ. In that regard, exemplary Relevant Cells that can be incorporated into tissue constructs of the presently-disclosed subject matter include neurons, cardiomyocytes, myocytes, chondrocytes, pancreatic acinar cells, islets of Langerhans, osteocytes, hepatocytes, Kupffer cells, fibroblasts, myoblasts, satellite cells, endothelial cells, adipocytes, preadipocytes, biliary epithelial cells, and the like. These types of cells may be isolated and cultured by conventional techniques known in the art. Exemplary techniques can be found in, among other places; Freshney, Culture of Animal Cells, A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559,022.

Furthermore, one of ordinary skill in the art will appreciate that such stromal cells, stem cells, and/or Relevant Cells can be incorporated into the prevascularized constructs during or after preparation. For example, microvessel fragments, stem cells, Relevant Cells, and/or stromal cells can be combined with an unpolymerized, matrix material, such as collagen, fibrin, or the like, prior to polymerizing the construct in an exemplary biochamber. Exemplary combinations of appropriate stem cells, stromal cells, and Relevant Cells for incorporation into microvascular constructs include: islets of Langerhans and/or pancreatic acinar cells for repairing the vasculature of a damaged pancreas; hepatocytes, hepatic progenitor cells, Kupffer cells, endothelial cells, endodermal stem cells, liver fibroblasts, and/or liver reserve cells for repairing the vasculature of a damaged liver; cardiomyocytes, Purkinje cells, pacemaker cells, myoblasts, mesenchymal stem cells, satellite cells, adipose-derived cells, stromal vascular fractions, and/or bone marrow stem cells for repairing the vasculature of a damaged or ischemic heart (see, e.g., Atkins et al., J. of Heart and Lung Transplantation, December 1999, at pages 1173-80; Tomita et al., Cardiovascular Research Institute, American Heart Association, 1999, at pages 92-101; Sakai et al., Cardiovascular Research Institute, American Heart Association, 1999, at pages 108-14); and the like.

For additional guidance regarding the types of cells that may be incorporated into a vascularized tissue construct, as well as methods for forming a microvascular construct, see U.S. Pat. No. 7,029,838, which is incorporated herein by this reference.

Figures 3, 6A:
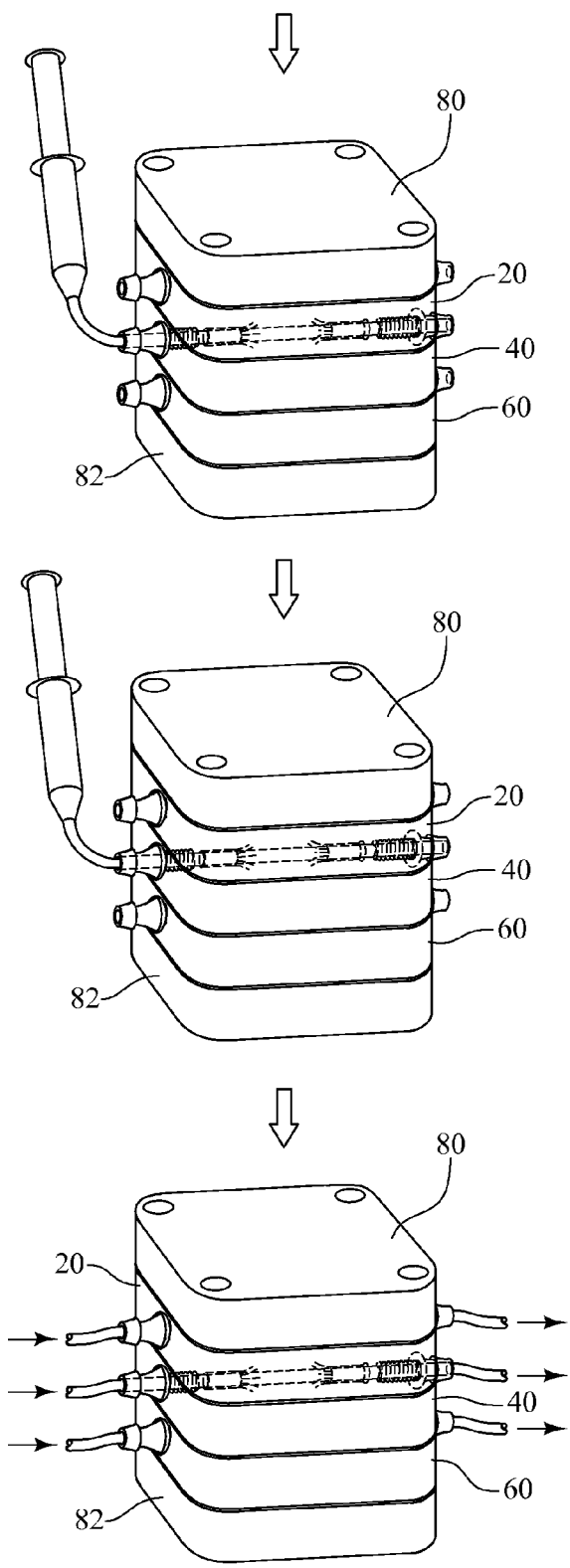
FIGS. 6A-6B are a schematic diagram and a workflow diagram, respectively, illustrating an exemplary method for vascularizing a tissue construct in accordance with the presently-disclosed subject matter.
Figures 3, 6B:
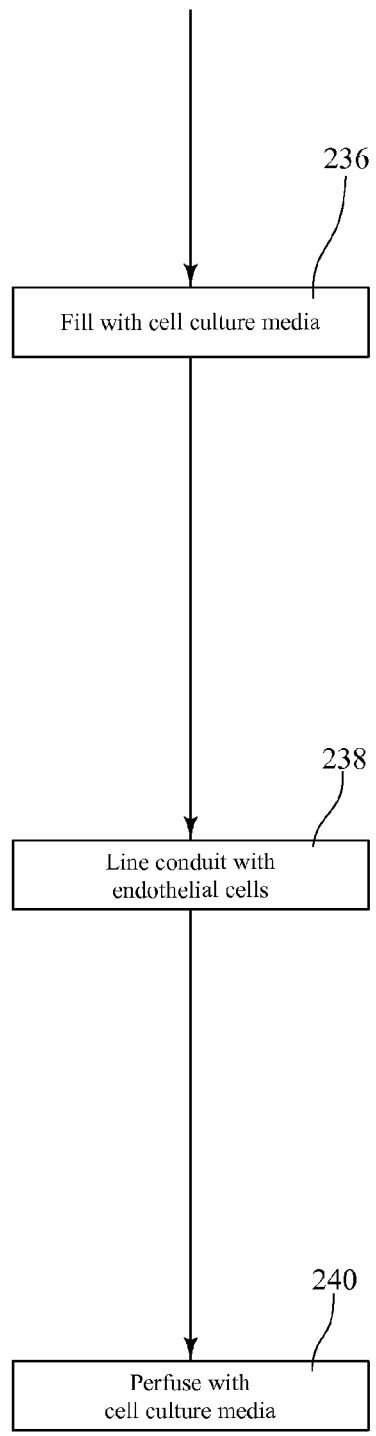

As noted, further provided, in some embodiments of the presently-disclosed subject matter, are methods for vascularizing a tissue construct. Referring now to FIGS. 6A and 6B, an exemplary method for vascularizing a tissue construct is provided in which an exemplary bioreactor, such as the bioreactor described above with reference to FIGS. 1 and 2, is initially provided, as indicated by step 200 in FIG. 6B. In this exemplary implementation, after the bioreactor 10 and its associated biochambers 20,40,60 has been provided, a tissue construct 100 is then positioned within the centrally-disposed cavity 44 of the intermediate biochamber 40, as indicated by steps 228 and 230 in FIG. 6B. Once the tissue construct 100 is sufficiently positioned within the intermediate biochamber 40, the bioreactor 10 is assembled together. The upper biochamber 20 and the lower biochamber 60 are then perfused with a cell culture media for a predetermined time period such that the tissue construct 100 is indirectly perfused over the external surfaces of the construct 100 and undergoes vascularization, as indicated by step 240 in FIG. 6B.

Typically, the tissue constructs are perfused with a standard cell culture media without the addition of growth factors for a time period sufficient to allow the vascular fragments within the construct to undergo vascularization and form a vascular network within the matrix. In some embodiments, this predetermined time period is about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, or longer as may be necessary to develop a vascular network in a particular construct and/or for a particular application.

Referring still to FIGS. 6A and 6B, and as discussed above with reference to FIGS. 3 and 4, with respect to the positioning of a tissue construct 100 within the centrally-disposed cavity 44 of the intermediate biochamber 40, in some embodiments, the positioning of the tissue construct 100 is performed by first positioning a support screen 50 in the centrally-disposed cavity 44 of the intermediate biochamber 40, as indicated by step 222 in FIG. 6B. Then, one or more connectors 56,58 are inserted within the centrally disposed cavity 44 of the intermediate biochamber 40 such that the connectors 56,58 are aligned with the inflow port 46, the outflow port 48, or both the inflow port 46 and the outflow port 48 of the intermediate biochamber 40, as indicated by step 224 in FIG. 6B. After the connectors 56,58 are inserted into the centrally-disposed cavity of the intermediate biochamber 40, a mandrel 51, such as a poly(tetrafluoroethylene) mandrel or mandrel comprised of another suitable material, is then inserted through the inflow port 46 and the outflow port 48 of the intermediate biochamber 40 such that the mandrel 51 extends through the one or more connectors 56,58, the support screen 50, and the centrally-disposed cavity 44, as indicated by step 226 in FIG. 6B.

Once the intermediate biochamber 40 and its associated components have been assembled, the tissue construct 100 is then added to the centrally-disposed cavity 44 of the intermediate biochamber 40. In some embodiments, and as indicated by step 227 in FIG. 6B, the step of adding the tissue construct 100 to the centrally-disposed cavity of the intermediate biochamber 40 is performed by first placing the intermediate biochamber 40 on an appropriate surface, such as a petri dish, a lower cover 82, or other flat surface, and then sealing the intermediate biochamber 40 to the surface using a hydrogel, or other gel, such that the construct does not leak out of the centrally-disposed cavity 44 when it is added to the intermediate biochamber 40, as indicated by step 227 in FIG. 6B. Once the biochamber 40 is sufficiently sealed to a surface, the tissue construct is then added in liquid form (e.g., a tissue construct comprised of microvascular fragments in cold, unpolymerized collagen) to the centrally-disposed cavity 44 of the intermediate biochamber 40 so that it fills the centrally-disposed cavity and surrounds the mandrel 51, as specified by step 228 in FIG. 6B. Following the addition of the unpolymerized construct 100, the construct 100 is then allowed to polymerize within the centrally-disposed cavity 44 of the intermediate biochamber 40, as indicated by step 230 in FIG. 6B. Once the construct 100 has polymerized, the intermediate biochamber 40 is removed from the flat surface and the mandrel 51 is also removed such that the tissue construct 100 defines a conduit 54 that extends through the tissue construct 100 and is in fluid communication with the inflow port 46 and the outflow port 48 of the intermediate biochamber 40, as indicated by step 232 in FIG. 6B. At this point, the intermediate biochamber 40 can then be assembled with the upper biochamber 20 and the lower biochamber 60 and filled with cell culture media, as indicated by steps 234 and 236, respectively, in FIG. 6B. Following assembly, the bioreactor 10 can then be perfused with a cell culture media to allow the construct to undergo vascularization, as indicated by step 240 in FIG. 6B.

As a further refinement, in some embodiments of the presently-disclosed methods, prior to perfusing an exemplary bioreactor 10 with a cell culture media, the conduit 54 is lined with a plurality of endothelial cells. In this regard, the endothelial cells can first be isolated from appropriate source, such as adipose-derived microvascular tissue (see, e.g., U.S. Pat. Nos. 4,820,626; 4,883,755; 5,035,708; and 5,957,972; each of which is incorporated herein by this reference), and delivered to the conduit 54 by perfusing a suspension of the endothelial cells into the conduit 54, as indicated by step 238 in FIG. 6B. By delivering the endothelial cells to the conduit 54, the cells line the conduit 54 and subsequently migrate into the surrounding construct 100 such that the endothelial cells not only form a conduit lining, but also form contiguous vascular-like branches with the vascular fragments contained within the construct 100. In this regard, an exemplary tissue construct 100 can thus be removed from the bioreactor 10, once it has sufficiently vascularized, and simply sewn in-line with an existing blood vessel in a host or used as an arteriovenous (AV) shunt in order to repair or replace a tissue that contains a compromised or damaged vasculature.

As yet another refinement, and as discussed above with reference to FIGS. 3 and 4, in some embodiments of the presently-disclosed methods for vascularizing a tissue construct, the one or more connectors 56,58 that are inserted within the centrally-disposed cavity 44 of the intermediate biochamber 40 are flared connectors in which the flared end of the connectors 56,58 extend into and engage the tissue construct. In some embodiments, the flared connectors 56,58 are comprised of a suturable material such that the microvascular construct 100 can easily be removed from an exemplary bioreactor 10 and sewn in-line with an existing blood vessel in a subject via the connectors 56,58. Exemplary suturable materials that can be used to fabricate a connector 56 or 58 of the presently-disclosed subject matter include, but are not limited to, materials such as electrospun biological, synthetic, or biological blends; polytetrafluoroethylene (PTFE); expanded polytetrafluoroethylene (ePTFE); DACRON™, vicryl, and the like. In some embodiments, these materials can be used to fabricate exemplary connectors 56,58 by themselves or, alternatively, these materials can be formed around an interior support structure, such as a stent.

As noted, an exemplary implementation of a method for vascularizing a tissue construct includes perfusing the tissue construct 100 by perfusing the upper biochamber 20 and the lower biochamber 60 with a cell culture media such that the tissue construct 100 is indirectly perfused over its external surfaces and undergoes vascularization. It has been discovered that by indirectly perfusing an exemplary tissue construct 100 over its external surface, the vascular fragments within the construct 100 undergo a greater degree of vascularization as evidenced by increases in the density of microvessels within an exemplary construct 100 and by increases in the sprouting of new vessels from the vascular fragments. However, it has also been discovered that perfusion through the conduit 54 in the intermediate biochamber 40 acts to maintain the viability of the developing vessels and to mature the vessels into a healthy network of vessels. As such, in certain embodiments of the presently-disclosed methods, a method of vascularizing a tissue construct is provided that further comprises perfusing the intermediate biochamber with a cell culture media for a predetermined time period such that the tissue construct 100 is directly perfused to maintain the viability of and to mature the vessels.

The presently-disclosed subject matter is further illustrated by the following specific but non-limiting examples.

EXAMPLES

Example 1

Microvessel Fragment Isolation

Microvessel fragments (MVFs) were isolated following previously described procedures (3,8). Briefly, epididymal fat pads were harvested from retired Sprague-Dawley male breeder rats, minced, and digested for approximately 7 min with 2 mg/mL collagenase (Worthington Biochemical Company, NJ, lot #46B8556) prepared in divalent cation free phosphate buffered saline (DCF-PBS) with 0.1% bovine serum albumen (Invitrogen, CA) (BSA-PBS). After centrifugation and 3 rinses with BSA-PBS, fragments were filtered sequentially through 2 sterile, nylon screens (20 µm and 500 µm pore size, respectively). MVFs were then collected in BSA-PBS by centrifugation and kept on ice until used.

Sterile, acidified rat tail collagen Type I (BD Biosciences) (greater than 4 mg/mL) was mixed with ice cold 4× Dulbecco's Modified Eagle's Media (DMEM) (Invitrogen) to yield a final concentration of 3 mg/mL collagen and 1×DMEM. The collagen pH was adjusted to 7.4 by the addition of 1N NaOH (as needed). MVFs were then suspended in the cold, neutralized collagen solution at a density of $2\times10^5$ fragments/mL. MVF-collagen suspensions remained on ice until use.

Example 2

Bioreactor Assembly and Perfusion

An exemplary bioreactor, such as the exemplary bioreactor depicted in FIGS. 1-4, was designed as a reconfigurable, multi-module system for supporting the culture of soft tissues. All bioreactor components were autoclaved prior to use. Consistent with the exemplary method depicted in FIGS. 6A and 6B, using aseptic technique, the support components (support screen, flared connectors (poly(tetrafluoroethylene)), and polymer mandrel (20 gauge poly(tetrafluoroethylene), Small Parts Inc., FL) were placed within the intermediate biochamber. A bioreactor cover was then placed in a petri dish before a hydrogel (Pluronic F-127, 30 weight % in DCF-PBS) was applied to the bottom of the intermediate biochamber. The gel-covered surface of the intermediate biochamber was then immediately placed on the cover within the petri dish and provided a seal to prevent collagen leakage. Three milliliters of a MVF-collagen suspension was then delivered to the centrally-disposed cavity of the intermediate biochamber and surrounded the mandrel. The intermediate biochamber was then placed in a tissue culture incubator and the suspension was allowed to polymerize for 60 minutes. After polymerization, the upper and lower biochambers were added to the assembly and the bioreactor was bolted together. The central polymer mandrel was slowly removed, forming an artificial conduit within the microvascular construct. Each biochamber was then connected to a perfusion line comprised of gas permeable tubing and a media reservoir. The biochambers were then perfused with cell culture media (low Glucose DMEM (Invitrogen, CA) media with 10% Fetal Bovine Serum (Gemini Bioproducts, CA), 1% penicillin/streptomycin (Invitrogen, CA) and 0.13% Fungizone (Invitrogen, CA)). For experimental analysis, 12 total bioreactors were perfused for 10 days.

Earlier work with microvascular constructs typically involved MVF seeding densities of 15,000 to 20,000 MVF per ml of collagen; and forming constructs of 100 to 500 µl volumes. These constructs were cultured in well-plates under static conditions (i.e., the constructs were not exposed to media perfusion) in which culture media was replaced every 4 days (3,4,8). As previously described, the MVF undergo spontaneous sprouting and neovessel growth (3,4,8). In standard conditions (DMEM+10% fetal bovine serum), microvessel density is 62 (±2.1) microvessels per $\mu m^2$ with approximately 90% (±1.3%) MVF viability after 6 days of culture.

In an attempt to recreate the conditions of these static cultures in the bioreactors, two different chamber-perfusion protocols were evaluated. The first involved the perfusion of media through all three biochambers, such that the constructs were perfused indirectly over their external surfaces (E-perfused) by perfusing the upper and lower biochambers, and were perfused directly (I-perfused) through the central conduit in the intermediate biochambers. This perfusion scheme (E+I perfusion) represented full nutrient delivery. The second scheme involved indirect perfusion through only the upper and lower biochambers (E-perfused), and represented partial delivery of nutrients. Alternate perfusion protocols including trans-biochamber perfusion schemes (i.e., perfusing into the lower biochamber, through the intermediate biochamber, and out the upper biochamber) were also attempted. However, the resistance to media flow through the collagen construct in those configurations was too large, and the subsequent pressure differential displaced the construct from the intermediate biochamber.

Example 3

Culture of Microvessel Constructs in the Bioreactor

All constructs were formed with similar initial MVF densities, approximately 20,000 microvessel fragments per mL. However, after 10 days of culture in the bioreactor, there were clear MVF density differences between the constructs conditioned by the two different perfusion protocols. To assess these differences, the number of elements positive for GS1, an endothelial cell marker, and the number of vessels with lumens were counted in sections of the constructs. The cross-sectional area of each analyzed section was determined by first capturing digital images of each section. These images were then assembled and the area of each section was manually traced and then calculated with the Area Calculator plug-in for ImageJ (distributed by NIH). Vessel counts, lumen counts, and area calculation were repeated for 3 sections of each sample. Microvessel density (GS-1 positive structures) in the E-perfusion scheme (7.9±0.5 vessel elements/$mm^2$) was more than twice as high as that for the E+I scheme (2.9±0.3 vessel elements/$mm^2$) (FIG. 7A). In contrast, the relationship between the fractions of microvessels with clearly patent lumens in the E-perfusion schemes was opposite to that observed for densities (FIG. 7B). In the E+I-perfused constructs, 14.8±1.3% of the microvessels exhibited a clearly patent lumen as compared to just 5.3±0.6% of the microvessels in the E-perfused cultures. Interestingly, constructs cultured with both perfusion conditions had the same number of lumen-containing structures per area (FIG. 7C).

Given that the microvessels with patent lumens likely represent the parent MVF, this indicated that relatively similar numbers of parent MVFs persisted in the constructs from the initial seeding density.

The similar number of lumens in E– and E+I-perfused constructs also indicated that the additional microvessels present in the former can be due to non-patent new vessel growth. To address this, the relative extent of neovessel sprouting and growth in the two culture conditions was evaluated. Briefly, a scoring system was used to evaluate the sprouting characteristics of microvascular constructs and bioreactor conditioned E– and E+I perfused constructs. A score of 0 represented no visible sprouting of constituent vessels. A score of 1 represented fragments with a few small, scattered sprouts while a score of 2 described a construct with extensive sprouting, many of significant length. Three independent observers viewed randomized fluorescent images and scored each image individually. The scores were compiled and analyzed with a statistical package.

The extent of sprouting was considerably greater in the E-perfused cultures than in the E+I perfused cultures (FIG. 8B). Furthermore, as typically observed in the static cultures, neovessels within the E-perfused constructs bifurcated and inosculated with nearby neovessels. Unlike the E+I-condition, where sprouting was uniformly minimal throughout the construct, E-conditioned constructs contained regional differences in the extent of sprouting. In the E-perfused condition, angiogenesis was highest at the periphery of the construct and lowest in the region nearest to the non-perfused central conduit or lumen (FIG. 8A).

The differences in sprouting index did not correlate with microvessel viability. To assess microvessel viability, the construct viability was determined via fluorescent image analysis by a custom Matlab (Mathworks, MA) program. Samples were first assayed with LIVE/DEAD Viability/Cytotoxicity Kit and then imaged. Image pairs, a viable image (positive calcein AM staining) and non-viable image (positive ethidum homodimer-1) of the same field of view, were processed. The analysis used previously described automated thresholding and size-filtering methods, maintaining the integrity of microvascular structures (19). Fragment viability was expressed as a ratio of the live vessel count to the total structures obtained by overlaying the thresholded and size-selected structures within paired images. This ratio was expressed as a percentage and compared across groups. Despite small yet significant differences in viability between different regions of the constructs, overall microvessel viability between the two different conditions was not substantially different ($p=0.6203$; FIG. 8C).

The differences in the results observed with the two perfusion protocols indicate that the potential shortcomings in culture conditions, assumed to be present in the E-perfusion protocol, are important in inducing angiogenesis from intact microvessel fragments in vitro, possibly by de-stabilizing the vessels. Conversely, conditions that support tissue health, such as those present in the E+I-perfusion scheme, act to stabilize and mature the microvessels. Furthermore, in addition to the implications on the relationship between microvessel stability and angiogenesis, these particular findings indicate that it can be possible to control angiogenesis in tissue constructs by modulating the level of de-stabilizing stress to the system. When angiogenesis is desired, the system can be stressed (e.g., by reducing perfusion to the bioreactor). Subsequently, re-establishing high levels of perfusion can then act to return the system to a stable situation and mature the forming neovessels.

Example 4

Modeling of Oxygen Diffusion within Bioreactor Microvascular Constructs

The difference in the angiogenic response in the bioreactor suggested that concentrations of essential factors within the constructs were different in the E– and E+I perfusion protocols. Focusing on the differences in sprouting between the two conditions, it was first hypothesized that a decrease in oxygen availability within E-perfused constructs led to increased angiogenic sprouting. To begin testing this hypothesis, an analysis of oxygen mass-transport in a bioreactor was performed by designing a finite element (FE) computer model that incorporated the unique geometry of the construct. Briefly, the bioreactor construct geometry was discretized into a hexahedral finite element mesh with 25,920 elements using TrueGrid (XYZ Scientific, CA) software. A mesh convergence study was used to determine this optimal mesh density. The mesh was imported into the ABAQUS finite element framework and assigned a transient mass diffusion constitutive model. This constitutive model required two parameters: mass concentration and the diffusion coefficient. The media oxygen concentration was prescribed to be the partial pressure for oxygen in water ($3.712 \times 10^{-8}$ g/mm$^3$). The initial concentration of oxygen in the collagen was assumed to be zero. The diffusion coefficient of oxygen in collagen was calculated to be $D_{O2}=2.286 \times 10^{-3}$ mm$^2$/s. Due to the low volume ratio of microvessels to collagen and the low metabolic rate of endothelial cells, oxygen consumption was assumed to be negligible. Additionally, the flow rate for the perfusion ports was low enough to ignore effects of turbulence and advection. Longitudinal and axial cross-sections were provided for simulations at 6, 12, and 18 hours, allowing internal comparisons of oxygen diffusion.

According to the computational model, oxygen levels within the bioreactor constructs equilibrated to those in the media (assumed 21%) within 48 hours regardless of the perfusion scheme (FIG. 9). However, it took approximately 1.3 hours longer to reach 50% equilibrium and 2.8 hours longer for 75% equilibrium in E-perfused constructs. Furthermore, results of the simulations suggest that oxygen gradients formed and persisted longer within the region in which sprouting was most prevalent in the E-perfused constructs. Additionally, the region nearest the central conduit or lumen remained hypoxic for the longest period of time in the E-perfused constructs.

Example 5

Angiogenesis in Microvascular Constructs

Based on the simulations, it was hypothesized that the difference in sprouting angiogenesis between the E– and E+I-perfused constructs may be due to some degree of hypoxic insult. To test this, microvessels were immunostained within E– and E+I-perfused constructs for the presence of a hypoxia marker, hypoxia inducible factor-1α (HIF1α) (9). Microvessels, including neovessels, present only in the E-perfused constructs stained positively for HIF1α. Immunostaining was particularly prevalent in the outer region of the construct in the P-perfused cultures, which is the zone exhibiting the highest index of sprouting (ROI3 in FIG. 8A).

To further investigate the effects of hypoxia on MVF angiogenesis, microvascular constructs (MVC) were cultured under static conditions and exposed to standard (21%

$O_2$) or hypoxic (1% $O_2$) conditions. Microvessels in both conditions stained positive for HIF1α indicating that even microvessels under the standard, assumed "normoxic" (i.e., 21% oxygen), conditions were experiencing hypoxic stress. As expected, MVF cultured under standard conditions exhibited considerable sprouting and neovessel growth (FIG. 10) (3,4,8). In contrast, MVF cultured in 1% oxygen conditions, sprouted very little or not at all and no neovessel growth was observed. Additionally, MVF cultured under hypoxic conditions exhibited reduced viability, but only later in the culture period (FIG. 11). This delayed viability decrease indicated that the level of hypoxia in the 1% oxygen conditions was too detrimental to MVF health and integrity for angiogenesis to occur. Given that sprouting occurred from and HIF1α was expressed in microvessels of standard, static MVC and the E-perfused constructs in the bioreactor, it was thus taken that the level of hypoxic stress was similar in both culture conditions.

Example 6

Microvessel Sprouting in Cultures and the Dependence on Growth Factors

The expression of HIF1α by MVF in the static and E-perfused constructs suggested that downstream autocrine vascular endothelial growth factor (VEGF) may explain the accompanying angiogenesis within the microvascular constructs (9,10,11). Therefore, to assess the role of two common isoforms of VEGF (VEGF-A and VEGF-B), a cocktail of soluble VEGFR1 and R2 (12) or a small molecule inhibitor of VEGF signaling, Cyclo-VEGI (13), was included in the culture media of standard, static MVC cultures. Neither the soluble VEGFR1/R2 cocktail nor the Cyclo-VEGI prevented MVF sprouting in static constructs; indicating that microvessel sprouting was independent of VEGF. This was corroborated by the lack of VEGFR2 activation (phosphorylation) in the samples by western blotting and is in accordance with the lack of change in mRNA levels for both VEGF and VEGFR in the static cultures throughout the culture period (14).

Throughout this document, various references are mentioned. All such references are incorporated herein by reference, including the references set forth in the following list:

REFERENCES

1. Secomb, T. W. & Pries, A. R. Information transfer in microvascular networks. Microcirculation 9, 377-387 (2002).
2. Folkman, J. Angiogenesis: an organizing principle for drug discovery? Nat Rev Drug Discov 6, 273-286 (2007).
3. Hoying, J. B., Boswell, C. A. & Williams, S. K. Angiogenic potential of microvessel fragments established in three-dimensional collagen gels. In Vitro Cell Dev Biol Anim 32, 409-419 (1996).
4. Shepherd, B. R. et al. Rapid perfusion and network remodeling in a microvascular construct after implantation. Arterioscler Thromb Vasc Biol 24, 898-904 (2004).
5. Frerich, B., Zueckmantel, K. & Hemprich, A. Microvascular engineering in perfusion culture: immunohistochemistry and CLSM findings. Head Face Med 2, 26 (2006).
6. Jain, R. K., Au, P., Tam, J., Duda, D. G. & Fukumura, D. Engineering vascularized tissue. Nature biotechnology 23, 821-823 (2005).
7. Ko, H. C., Milthorpe, B. K. & McFarland, C. D. Engineering thick tissues—the vascularisation problem. European cells & materials 14, 1-18; discussion 18-19 (2007).
8. Chang, C. C. & Hoying, J. B. Directed three-dimensional growth of microvascular cells and isolated microvessel fragments. Cell transplantation 15, 533-540 (2006).
9. Yamakawa, M. et al. Hypoxia-inducible factor-1 mediates activation of cultured vascular endothelial cells by inducing multiple angiogenic factors. Circulation research 93, 664-673 (2003).
10. Jensen, R. L., Ragel, B. T., Whang, K. & Gillespie, D. Inhibition of hypoxia inducible factor-1alpha (HIF-1alpha) decreases vascular endothelial growth factor (VEGF) secretion and tumor growth in malignant gliomas. Journal of neuro-oncology 78, 233-247 (2006).
11. Yancopoulos, G. D. et al. Vascular-specific growth factors and blood vessel formation. Nature 407, 242-248 (2000).
12. Ferrara, N. et al. Vascular endothelial growth factor is essential for corpus luteum angiogenesis. Nature medicine 4, 336-340 (1998).
13. Zilberberg, L. et al. Structure and inhibitory effects on angiogenesis and tumor development of a new vascular endothelial growth inhibitor. J Biol Chem 278, 35564-35573 (2003).
14. Krishnan, L., Hoying, J. B., Nguyen, H., Song, H. & Weiss, J. A. Interaction of angiogenic microvessels with the extracellular matrix. Am J Physiol Heart Circ Physiol 293, H3650-3658 (2007).
15. Bishop, A. Role of oxygen in wound healing. Journal of wound care 17, 399-402 (2008).
16. Jain, R. K. Molecular regulation of vessel maturation. Nature medicine 9, 685-693 (2003).
17. Pepper, M. S. Manipulating angiogenesis. From basic science to the bedside. Arterioscler Thromb Vasc Biol 17, 605-619 (1997).
18. Salzmann, D. L., Kleinert, L. B., Berman, S. S. & Williams, S. K. Inflammation and neovascularization associated with clinically used vascular prosthetic materials. Cardiovasc Pathol 8, 63-71 (1999).
19. Krishnan, L. et al. Effect of mechanical boundary conditions on orientation of angiogenic microvessels. Cardiovascular research 78, 324-332 (2008).
20. Ramsey, F. L. & Schafer, D. W. The statistical sleuth: a course in methods of data analysis. 2nd edn, (Duxbury/Thomson Learning, 2002).
21. Ramanujan, S. et al. Diffusion and convection in collagen gels: implications for transport in the tumor interstitium. Biophysical journal 83, 1650-1660 (2002).
22. Embryonic Stem Cells, Methods and Protocols, Turksen, ed., Humana Press (2002).
23. Weisman et al., Annu Rev. Cell. Dev. Biol. 17:387-403.
24. Pittinger et al., Science, 284:143-47 (1999).
25. Animal Cell Culture, Masters, ed., Oxford University Press (2000).
26. Jackson et al., PNAS 96(25):14482-86 (1999).
27. Zuk et al., Tissue Engineering, 7:211-228 (2001).
28. Prockop, Science, 276:71-74 (1997).
29. Theise et al., Hepatology, 31:235-40 (2000).
30. Atkins et al., J. of Heart and Lung Transplantation, p. 1173-80; December 1999.
31. Tomita et al., Cardiovascular Research Institute, American Heart Association, p. 92-101, 1999.
32. Sakai et al., Cardiovascular Research Institute, American Heart Association, p. 108-14, 1999.
33. Current Protocols in Cell Biology, Bonifacino et al., eds., John Wiley & Sons, 2000.
34. Freshney, Culture of Animal Cells, A Manual of Basic Techniques, 4th ed., Wiley Liss, John Wiley & Sons, 2000.
35. Basic Cell Culture: A Practical Approach, Davis, ed., Oxford University Press, 2002.

36. Animal Cell Culture: A Practical Approach, Masters, ed., 2000.
37. U.S. Pat. No. 4,963,489, to Naughton, et al., issued Oct. 16, 1990, and entitled "Three-Dimensional Cell and Tissue Culture System."
38. U.S. Pat. No. 4,820,626, to Williams, et al., issued Apr. 11, 1989, and entitled "Method of Treating a Synthetic or Naturally Occurring Surface with Microvascular Endothelial Cells, and the Treated Surface Itself."
39. U.S. Pat. No. 4,883,755, to Carabasi, et al., issued Nov. 28, 1989, and entitled "Method of Reendothelializing Vascular Linings"
40. U.S. Pat. No. 5,035,708 to Alchas, et al., issued Jul. 30, 1991, and entitled "Endothelial Cell Procurement and Deposition Kit."
41. U.S. Pat. No. 5,516,681 to Naughton, et al., issued May 14, 1996, and entitled "Three-Dimensional Pancreatic Cell and Tissue Culture System."
42. U.S. Pat. No. 5,559,022 to Naughton, et al., issued Sep. 24, 1996, and entitled "Liver Reserve Cells."
43. U.S. Pat. No. 5,672,346 to Srour, et al., issued Sep. 30, 1997, and entitled "Human Stem Cells Compositions and Methods."
44. U.S. Pat. No. 5,827,735 to Young, et al., filed Oct. 27, 1998, and entitled "Pluripotent Mensenchymal Stem Cells and Methods of Use Thereof"
45. U.S. Pat. No. 5,957,972 to Williams, et al., issued Sep. 28, 199, and entitled "Implants Possessing a Surface of Endothelial Cells Genetically Modified to Inhibit Intimal Thickening."
46. U.S. Pat. No. 7,029,838 to Williams, et al., issued Apr. 18, 2006, and entitled "Prevascularized Constructs to Provide Blood Perfusion."

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A modular bioreactor, comprising:
    an upper biochamber;
    a lower biochamber;
    an intermediate biochamber positioned between the upper biochamber and the lower biochamber; and
    a three-dimensional matrix;
    wherein each biochamber has an interior side wall defining a centrally-disposed cavity,
    wherein the interior side wall is continuous around the centrally-disposed cavity,
    wherein each biochamber defines an inflow port through the interior side wall and in fluid communication with the centrally-disposed cavity,
    wherein each biochamber defines an outflow port through the interior side wall and in fluid communication with the centrally-disposed cavity,
    wherein each biochamber is in fluid communication with adjacent biochambers, and
    wherein the three-dimensional matrix is positioned within the centrally-disposed cavity of the intermediate biochamber, provides a substrate for cells, and defines a conduit extending through the three-dimensional matrix and in fluid communication with the inflow port and the outflow port of the intermediate biochamber.
2. The modular bioreactor of claim 1, further comprising an upper cover and a lower cover.
3. The modular bioreactor of claim 1, wherein the inflow port and the outflow port of each biochamber are positioned on opposite sides of each biochamber.
4. The modular bioreactor of claim 1, further comprising a support screen positioned in the centrally-disposed cavity of the intermediate biochamber, wherein the three-dimensional matrix engages the support screen.
5. The modular bioreactor of claim 1, wherein the three-dimensional matrix includes collagen.
6. The modular bioreactor of claim 1, further comprising a first connector positioned within the centrally-disposed cavity of the intermediate biochamber and aligned with the inflow port and the conduit defined through the three-dimensional matrix.
7. The modular bioreactor of claim 6, wherein the first connector is a flared connector.
8. The modular bioreactor of claim 6, further comprising a second connector positioned within the centrally-disposed cavity of the intermediate biochamber and aligned with the outflow port and the conduit defined through the three-dimensional matrix.
9. The modular bioreactor of claim 8, wherein the second connector is a flared connector.
10. The modular bioreactor of claim 1, further comprising one or more spacers, each spacer having a centrally-disposed cavity in fluid communication with and positioned between the biochambers.
11. The modular bioreactor of claim 2, further comprising one or more spacers, each spacer having a centrally-disposed cavity in fluid communication with the biochambers and positioned between the upper biochamber and the upper cover, the lower biochamber and the lower cover, or both.
12. A system for vascularizing a tissue construct, comprising:
    a bioreactor having an upper biochamber, a lower biochamber, and an intermediate biochamber positioned between the upper biochamber and the lower biochamber, wherein each biochamber has an interior side wall defining a centrally-disposed cavity, wherein the interior side wall is continuous around the centrally-disposed cavity, wherein each biochamber defines an inflow port through the interior side wall and in fluid communication with the centrally-disposed cavity, and wherein each biochamber defines an outflow port through the interior side wall and in fluid communication with the centrally-disposed cavity;
    a three-dimensional tissue construct positioned within the cavity of the intermediate biochamber, the three-dimensional tissue construct defining a conduit extending through the three-dimensional tissue construct and in fluid communication with the inflow port and the outflow port of the intermediate biochamber; and
    a means for perfusing the bioreactor via selected inflow ports and outflow ports of the respective biochambers with a cell culture media, such that the tissue construct undergoes vascularization.
13. The system of claim 12, further comprising a first connector positioned within the centrally-disposed cavity of the intermediate biochamber and aligned with the inflow port and the conduit defined through the three-dimensional tissue construct.
14. The system of claim 13, wherein the first connector is a flared connector for engaging the three-dimensional tissue construct.
15. The system of claim 13, further comprising a second connector positioned within the centrally-disposed cavity of the intermediate biochamber and aligned with the outflow port and the conduit defined through the three-dimensional tissue construct.

16. The system of claim 15, wherein the second connector is a flared connector for engaging the three-dimensional tissue construct.

17. A method for vascularizing a tissue construct, comprising:
providing a bioreactor having an upper biochamber, a lower biochamber, and an intermediate biochamber positioned between the upper biochamber and the lower biochamber, wherein each biochamber has an interior side wall defining a centrally-disposed cavity, wherein the interior side wall is continuous around the centrally-disposed cavity, wherein each biochamber defines an inflow port through the interior side wall and in fluid communication with the centrally-disposed cavity, and wherein each biochamber defines an outflow port through the interior side wall and in fluid communication with the centrally-disposed cavity;
positioning a three-dimensional tissue construct within the cavity of the intermediate biochamber, the three-dimensional tissue construct defining a conduit extending through the three-dimensional tissue construct and in fluid communication with the inflow port and the outflow port of the intermediate biochamber; and
perfusing the upper biochamber and the lower biochamber via the inflow ports and the outflow ports of the respective biochambers with a cell culture media for a predetermined time period such that the tissue construct is indirectly perfused and undergoes vascularization.

18. The method of claim 17, wherein the three-dimensional tissue construct comprises a microvascular fragment incorporated into a matrix.

19. The method of claim 18, wherein the positioning of the three-dimensional tissue construct within the cavity of the intermediate biochamber comprises the steps of:
positioning a support screen in the centrally-disposed cavity of the intermediate biochamber;
inserting one or more connectors within the centrally-disposed cavity of the intermediate biochamber such that the connectors are aligned with the inflow port, the outflow port, or both the inflow port and the outflow port of the intermediate biochamber; and
inserting a mandrel through the inflow port and the outflow port of the intermediate biochamber such that the mandrel extends through the one or more connectors, the support screen, and the centrally-disposed cavity.

20. The method of claim 19, wherein the one or more connectors are flared connectors for engaging the three-dimensional tissue construct.

21. The method of claim 19, further comprising the steps of:
adding the three-dimensional tissue construct to the centrally-disposed cavity of the intermediate biochamber;
allowing the three-dimensional tissue construct to polymerize; and
removing the mandrel to thereby form the conduit through the three-dimensional tissue construct.

22. The method of claim 21, further comprising the step of lining the conduit with a plurality of endothelial cells.

23. The method of claim 18, further comprising perfusing the intermediate biochamber with the cell culture media for a predetermined time period such that the three-dimensional tissue construct is directly perfused to maintain viability and to mature the vessels.

24. A modular bioreactor, comprising:
an upper biochamber having a continuous interior side wall, the continuous sidewall of the upper biochamber defining a centrally-disposed cavity of the upper biochamber and further defining an inflow port and an outflow port in fluid communication with the centrally-disclosed cavity of the upper biochamber;
a lower biochamber having a continuous interior side wall, the continuous sidewall of the lower biochamber defining a centrally-disposed cavity of the lower biochamber and further defining an inflow port and an outflow port in fluid communication with the centrally-disclosed cavity of the lower biochamber;
an intermediate biochamber positioned between the upper biochamber and the lower biochamber and having a continuous interior side wall, the continuous sidewall of the intermediate biochamber defining a centrally-disposed cavity of the intermediate biochamber and further defining an inflow port and an outflow port in fluid communication with the centrally-disclosed cavity of the intermediate biochamber;
a support screen extending along the continuous side wall defining the centrally-disposed cavity of the intermediate biochamber, the circumferential support screen for engaging a three-dimensional matrix positioned within the centrally-disposed cavity of the intermediate biochamber;
a first connector positioned within the inflow port of the intermediate biochamber and configured to engage the three-dimensional matrix; and
a second connector positioned within the outflow port of the intermediate biochamber and configured to engage the three-dimensional matrix.

25. The modular bioreactor of claim 24, wherein the support screen is circumferential.

* * * * *